(12) United States Patent
Martin et al.

(10) Patent No.: US 7,476,217 B2
(45) Date of Patent: Jan. 13, 2009

(54) INJECTION DEVICE

(75) Inventors: Jeffrey Martin, Barnet (GB); Martin Lawrence Hughes, Bucks (GB)

(73) Assignee: Cilag GmbH International, Zug (CH)

( * ) Notice: Subject to any disclaimer, the term of this patent is extended or adjusted under 35 U.S.C. 154(b) by 315 days.

(21) Appl. No.: 10/513,159

(22) PCT Filed: May 2, 2003

(86) PCT No.: PCT/GB03/01946

§ 371 (c)(1),
(2), (4) Date: Feb. 2, 2005

(87) PCT Pub. No.: WO03/092771

PCT Pub. Date: Nov. 13, 2003

(65) Prior Publication Data

US 2005/0124940 A1  Jun. 9, 2005

(30) Foreign Application Priority Data

May 2, 2002  (GB) .................................. 0210123.6
Dec. 17, 2002  (GB) .................................. 0229384.3

(51) Int. Cl.
*A61M 5/00* (2006.01)
(52) U.S. Cl. ..................................................... 604/181
(58) Field of Classification Search .......... 604/154–243
See application file for complete search history.

(56) References Cited

U.S. PATENT DOCUMENTS

| 2,019,382 | A | * | 10/1935 | Aronson | 431/127 |
| 4,561,856 | A | | 12/1985 | Cochran | |
| 6,045,534 | A | | 4/2000 | Jacobsen et al. | |
| 6,258,068 | B1 | | 7/2001 | Kirchhofer et al. | |
| 6,371,939 | B2 | * | 4/2002 | Bergens et al. | 604/156 |
| 2001/0005781 | A1 | | 6/2001 | Amark et al. | |
| 2001/0021826 | A1 | | 9/2001 | Fischer et al. | |
| 2001/0021828 | A1 | | 9/2001 | Fischer et al. | |
| 2001/0049496 | A1 | | 12/2001 | Jost et al. | |
| 2004/0019326 | A1 | * | 1/2004 | Gilbert et al. | 604/135 |

FOREIGN PATENT DOCUMENTS

| DE | 44 28 467 A | 2/1996 |
| GB | 143 084 A | 5/1920 |
| WO | WO 95/35126 A | 12/1995 |
| WO | WO 03/097133 A1 | 11/2003 |

\* cited by examiner

*Primary Examiner*—Kevin C Sirmons
*Assistant Examiner*—Deanna K Hall
(74) *Attorney, Agent, or Firm*—Foley & Lardner LLP

(57) ABSTRACT

An injection device is for use with a syringe having a bore extending from an end surface, a needle communicating with the bore through the end surface and a dispensing piston movable in the bore towards the end surface. The injection device includes a housing having an opening, a resilient member for biasing the syringe and needle inwardly of the housing, a drive element movable towards the one end so as to move the needle out of the opening against the bias of the resilient member, a delatch mechanism operable to release the syringe such that the needle moves inwardly of the housing, and a drive coupling. The drive coupling gradually reduces in length such that, after the drive element has moved the dispensing piston to the end surface, the drive element continues to move to the dispensing piston at the end surface.

57 Claims, 18 Drawing Sheets

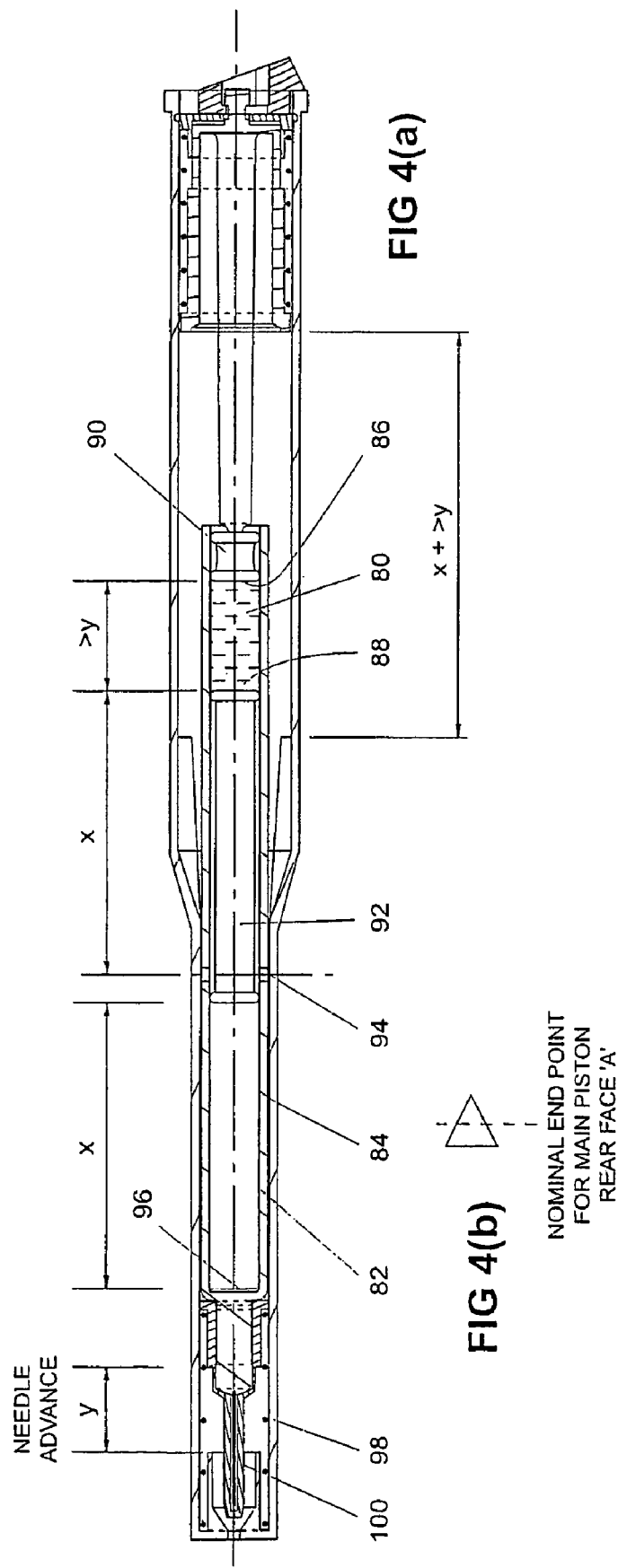

INJECTION DEVICE

The present application is a National Phase Application of PCT/GB03/01946 titled "Injection Device" and filed on May 2, 2003, which published under PCT Article 21(2) on Nov. 13, 2003 as WO 03/092771 A1, and which claims priority to British Patent Application Nos. 0210123.6 filed on May 2, 2002, and 0229384.3 filed on Dec.17, 2002.

The present invention relates to an injection device, in particular an injection device which, having dispensed the contents of a syringe, automatically retracts the needle of the syringe.

BACKGROUND

Devices exist which are spring loaded to extend automatically the needle of a syringe from the device, dispense the contents of the syringe and then automatically retract the needle. WO 95/35126 describes such a device.

As illustrated in FIG. 1 of the accompanying drawings, the device includes a housing 2 in which a syringe 4 is contained. The housing 2 includes an opening 6 through which the needle 8 of the syringe 4 may extend. A retraction spring 10 biases the syringe 4 away from the opening 6. The device also includes a drive element 12 which is biassed by a spring 14 to drive a coupling 16 to move the dispensing piston 18 of the syringe 4. In use, a release mechanism 20 releases the drive element 12 such that the syringe 4 is first moved forwards and the needle 8 projects through the opening 6. Subsequently, the dispensing piston 18 is moved so as to expel the contents of the syringe 4. The device is designed to include a delatch mechanism. In particular, at the point at which the dispensing piston 18 reaches the end of the bore in the syringe 4, arms 22 at the end of the coupling 16 are deflected by a collar 24 within the housing 2 so as to disengage from the drive element 12. The arms 22 and coupling 16 may then move within a central passage of the drive element 12. As a result, by virtue of the bias of spring 10, the coupling 16 moves inside the drive element 12, the syringe 4 is driven away from the opening 6 and the needle 8 is retracted within the opening 6.

Other similar delatch or retract arrangements have also been proposed. For instance, EP-A-0 516 473 discloses one embodiment in which, at the point at which the dispensing piston reaches the end of the bore in the syringe, a portion of the coupling instantaneously collapses in length as the retraction spring retracts the needle of the spring.

In practice, all of these proposals suffer a problem that, due to a stack up of tolerances of the various manufactured components of the assembled device (the dimensions of all manufacture components vary around a mean), it cannot be assured that the delatch mechanism will enable retraction of the syringe and needle at precisely the moment at which the dispensing a piston reaches the end of the bore. In practice, either the mechanism delatches before the dispensing piston reaches the end of the bore, such that the syringe is not emptied, or the piston reaches the end of the bore before the mechanism has moved sufficiently far to delatch.

Although this problem has been recognised before, for instance in U.S. Pat. No. 6,159,181, the proposed solution has been to provide a user actuated retraction mechanism rather than an automatic one. This is considered to be undesirable.

SUMMARY

It is an object of the present invention to provide an injection device which is relatively simple and of low cost (so as to be useful as a single use device) and which overcomes or at least reduces the problems identified above.

According to the present invention there is provided an injection device including:

a housing for containing a syringe having a bore extending from an end surface, a needle communicating with the bore through the end surface and a dispensing piston movable in said bore towards said end surface so as to expel the contents of the syringe through the needle, the housing having an opening at one end through which the needle may extend;

a resilient member for biassing the syringe and needle inwardly of the housing;

a drive element movable towards said one end so as to move the needle of the syringe out of the opening, preferably against the bias of the resilient member, and to move the dispensing piston of the syringe towards the end surface;

a mechanism, such as a delatch or retract mechanism, operable to release the syringe such that the needle moves inwardly of the housing;

a drive coupling for extending from said drive element to the dispensing piston of the syringe so as to transfer movement of said drive element to the dispensing piston; wherein the drive coupling is compressible in length, preferably whilst overcoming the bias of the resilient member, such that, after the drive element has moved the dispensing piston to the end surface, the drive coupling gradually reduces in length whilst the dispensing piston is maintained at the end surface until said mechanism releases the syringe.

According to the present invention there is also provided a drive coupling for use in an injection device, the drive coupling having:

a length for extending from the drive element to the dispensing piston of the syringe so as to transfer movement of the drive element to the dispensing piston; wherein the drive coupling is compressible in length, preferably whilst overcoming the bias of the resilient member, such that, after the drive element has moved the dispensing piston to the end surface, the drive coupling gradually reduces in length whilst the dispensing piston is maintained at the end surface until the mechanism releases the syringe.

Thus, since the drive coupling is able to gradually reduce in length whilst maintaining the needle in its extended position, it is possible to design the injection device to operate the mechanism at some point after the dispensing piston has reached the end surface and fully expelled the contents of the syringe. Since the mechanism is now triggered at some uncritical point of time after the contents of the syringe have been expelled, tolerances of the various components are no longer a problem. Preferably, the drive coupling is capable of reducing in length whilst providing a resistive force to overcome the resilient member.

It will be appreciated that the length of the drive coupling here is the effective length, ie the length measured from the drive element to the dispensing piston, such that, according to the present invention, the length gradually decreases and the drive element moves relatively towards the dispensing piston. To produce this reduction in length, it is sufficient to provide components which are relatively movable in any way which allows the drive element to move towards the dispensing piston. Indeed, the drive coupling can be provided by a component which is movable in any way relative to the drive element which allows drive to and relative movement to the dispensing piston.

Preferably, the mechanism is operable when the drive element reaches a predetermined position in said housing and the drive coupling gradually reduces in length such that, after the dispensing piston reaches the end surface, the drive element continues to move in said housing to said predetermined position.

The drive element may continue to move over a period of time as the drive coupling continues to reduce in length such that, even though the dispensing piston has reached the end of its travel and abuts the end surface, the drive element can assuredly move to the necessary position to trigger the return mechanism. It is merely sufficient to ensure that the drive element does not reach the position for triggering the mechanism before the dispensing piston reaches the end surface of the syringe.

It will be appreciated that, contrary to previous mechanisms, in particular the collapsing structures of EP-A-0 516 473, the drive coupling of the present invention does not collapse instantaneously but reduces in length gradually. Indeed, the length of the drive coupling continues to reduce in length gradually even after the dispensing piston abuts the end surface. Furthermore, whilst collapsing, the drive coupling still transfers sufficient force to maintain the needle in its extended position and, preferably, overcome the bias of the retraction spring.

In contrast, at some point up to and including that at which the dispensing piston abuts the end surface, previous collapsing couplings collapse instantaneously under the influence of the retraction spring and do not resist its bias. In particular, once the collapsing coupling of EP-A-0 516 473 starts to reduce in length, it offers virtually no resistance to the retract spring and, hence, is almost instantaneously collapsed.

Furthermore, in previous arrangements, once the dispensing piston abuts the end surface, the drive element and drive coupling can move no farther and, hence, collapsing of the drive coupling cannot be initiated. However, with the present invention, even after the dispensing piston abuts the end surface, the drive element can continue to move whilst the dispensing piston is maintained at the end surface.

The present invention could be considered as a damped collapse of the drive coupling such that the force and motion of the drive element maintain the syringe and needle in position, even after the dispensing piston abuts the end surface, until the drive element reaches the predetermined position.

Depending on the exact nature of the arrangement, the drive coupling may only start to collapse when the dispensing piston reaches the end surface or it may start to collapse at some predetermined point just before the piston reaches the end surface. Before it starts to collapse, it is preferably rigid. A releasable latch may be provided to prevent any collapse of the drive coupling until the drive element and dispensing piston reach respective predetermined positions.

Provided that there is sufficient length and that the drive element causes the dispensing piston to expel the contents of the syringe sufficiently quickly, it is possible for the drive coupling to reduce in length gradually throughout the entire operation and the entire movement of the drive element. However, since the controlled collapsing of the drive coupling is only required in the region of the dispensing piston reaching the end surface, it is preferable that the drive coupling remains of constant length before then. Thus, preferably, the drive coupling does not reduce in length until the dispensing piston has reached a position at least proximate the end surface.

The drive coupling may include a chamber defined between first and second relatively movable walls, the first wall being movable by said drive element and said second wall being operable to move the dispensing piston, and a bleed orifice for bleeding flowable material, preferably from the chamber.

In this way, drive from the drive element and the first wall is transmitted through flowable material in the chamber to the second wall and the dispensing piston. By means of the bleed orifice, material may gradually bleed from the chamber such that, in a preferred embodiment, the first and second walls move gradually towards one another and the length of the drive coupling is reduced.

The flowable material merely has to provide the property of resisting flow through a restriction and need not be a true fluid but could be a Bingham plastic for example. In a preferred embodiment, the material is preferably a fluid such as a liquid or gas.

A bleed orifice could be included in the first wall so as to enable fluid to bleed from the fluid chamber when the drive element moves the first wall and compresses the drive coupling and fluid chamber.

The dimensions of any bleed orifice are chosen such that pressure of the fluid in the fluid chamber is maintained sufficient to force the dispensing piston to the end surface of the syringe.

Preferably, the drive coupling includes a main body for mounting on the syringe so as to have a position fixed relative to the bore and the needle, the main body having a bounding or peripheral wall defining an elongate passage within which the first and second walls are both movable, the fluid chamber being defined by the peripheral wall and the first and second walls.

In this way, as the drive element moves towards the first end, both the first and second walls are moved within the elongate passage, the fluid chamber being defined by the space between them.

A bleed orifice may be formed at a predetermined longitudinal position along the peripheral wall such that it is only exposed to the fluid chamber once the second wall passes the predetermined longitudinal position.

In this way, until the second wall reaches the predetermined longitudinal position, the fluid chamber remains of constant volume and the effective length of the drive coupling does not reduce. However, once the second wall reaches the predetermined longitudinal position, fluid bleeds through the bleed orifice so that the length between the first and second walls and the effective length of the drive coupling gradually reduces so as to ensure that the drive element triggers the delatch and retract mechanism.

It should be appreciated that the present invention can be applied to injection devices which house conventional syringes or which house other mass produced cartridges of a standard design. However, it is also possible to form the drive coupling in the syringe itself.

The first and second walls may be movable in the bore of the syringe such that the fluid chamber is defined by the bore and the first and second walls.

In this way, the number of component parts may be reduced.

The second wall may form an integral part of the dispensing piston or may drive the dispensing piston through a spacer or the like.

As described above, a bleed orifice could be formed in the first wall so as to enable fluid to bleed from the fluid chamber. However, preferably, the bleed orifice is formed at a predetermined longitudinal position along the bore and is only opened to the fluid chamber once the second wall passes the predetermined longitudinal position.

In this way, as described above, the fluid chamber remains of constant volume until the second wall reaches the predetermined longitudinal position such that the effective length of the drive coupling starts to reduce only in the region where the dispensing piston reaches the end surface.

The bleed orifice may be circular. Alternatively, it may have a cross-section which is elongate and/or there may be an array of bleed orifices extending towards the end surface such that as a second wall moves towards the end surface, fluid bleeds faster from the fluid chamber.

The orifices may be arranged in this way such that, once the dispensing piston reaches the end surface, the second wall exposes a sufficient area of the bleed orifice(s) to allow fluid to bleed from the fluid chamber at a rate appropriate to allow the resilient member to retract the syringe and needle.

Indeed, according to the present invention, there may be provided an injection device including:

a housing containing a syringe with a syringe body having a bore extending from an end surface, a needle communicating with the bore through the end surface and a dispensing piston movable in said bore towards said end surface so as to expel the contents of the syringe through the needle, the housing having an opening at one end through which the needle may extend;

a resilient member for biasing the syringe and needle inwardly of the housing;

a drive element movable towards said one end so as to move the needle of the syringe out of the opening, preferably against the bias of the resilient member, and to move the dispensing piston of the syringe towards the end surface; wherein the syringe further includes:

a secondary piston movable in said bore, the dispensing piston and the secondary piston defining a fluid filled chamber therebetween; and a bleed orifice communicating with said bore; wherein the bleed orifice is positioned at a distance from the end surface and the dispensing piston is of such a length that the dispensing piston exposes the bleed orifice to the fluid filled chamber as the dispensing piston reaches the end surface and loss of fluid from the fluid chamber allows retraction of the needle by virtue of the bias of the resilient member.

Since the point of retraction is only dependent on the position of the bleed orifice and the length of the dispensing piston, the number of tolerances affecting the point of retraction are reduced such that the syringe can be assuredly retracted at the point at which the contents is fully dispensed.

Alternatively, the drive coupling may include a drive frictional surface engaging a driven frictional surface, the drive frictional surface being movable by the drive element and the driven frictional surface being operable to move the dispensing piston such that, when the dispensing piston reaches the end surface, the first frictional surface slips relative to the second frictional surface.

Thus, in this case, the drive coupling only reduces in length once the dispensing piston reaches the end surface. The drive element continues to apply a force to the drive coupling by virtue of the frictional resistance such that the frictional surfaces slip, the drive coupling reduces in length and the drive element reaches the required position to trigger the return mechanism.

The drive frictional surface may be rotatable about an axis generally perpendicular to the surface and be moved by the drive element at a position offset from the axis.

Similarly, the driven frictional surface may be rotatable about an axis generally parallel to the surface and may be operable to move the dispensing piston from a position offset from the axis.

In other words, drive to or from the rotational frictional surface may be by means of a crank mechanism such that, when the surfaces slip and rotate, the connection points to the drive element and the dispensing piston move closer together.

The drive coupling may include a rack and a pinion gear wherein one of the rack and the pinion gear is movable by the drive element and the other of the rack and the pinion is operable to move the dispensing piston.

In this way, as the drive element exerts a compression force on the drive coupling, the rack will tend to rotate the pinion gear.

The pinion gear may include a friction brake to prevent rotation and allow the drive element to move the dispensing piston. When the dispensing piston reaches the end surface, the friction brake slips and the length of the drive coupling is reduced.

Alternatively, the pinion gear can drive a fly wheel such that when the dispensing piston reaches the end surface, the pinion gear is turned against the inertial resistance of the fly wheel. Thus, once again, the length of the drive coupling is reduced.

As explained above, previous injection devices drive the dispensing piston to first move the syringe as a whole and position the needle outside of the injection device housing. This works well for fine needles where the back pressure on the fluid for injection is relatively high and the force required to insert the needle is relatively low. However, where there is more difficulty in inserting the needle, there is a possibility that some fluid will be dispensed from the needle before it is correctly inserted below the skin.

Hence, preferably, the injection device further includes an engagement for transferring drive directly from the drive coupling to the syringe body such that movement of the drive element towards said one end causes no relative movement of the dispensing piston in the syringe wherein the engagement is releasable once the needle of the syringe extends out of the opening such that movement of the drive element towards said one end causes relative movement of the dispensing piston in the syringe body.

Thus, furthermore, according to the present invention, there is provided an injection device including:

a housing for containing a syringe having a bore extending in a syringe body from an end surface, a needle communicating with the bore through the end surface and a dispensing piston movable in said bore towards said end surface so as to expel the contents of the syringe through the needle, the housing having an opening at one end through which the needle may extend;

a drive element movable towards said one end so as to move the needle of the syringe out of the opening and to move the dispensing piston of the syringe towards the end surface;

a drive coupling for extending from said drive element to the dispensing piston of the syringe so as to transfer movement of said drive element to the dispensing piston; and an engagement for transferring drive directly from the drive coupling to the syringe body such that movement of the drive element towards said one end causes no relative movement of the dispensing piston in the syringe; wherein the engagement is releasable once the needle of the syringe extends out of the opening such that movement of the drive element towards said one end causes relative movement of the dispensing piston in the syringe body.

This ensures that the drive element correctly positions the syringe with the needle protruding from the housing before the dispensing piston is moved to dispense the contents of the syringe.

Preferably, the injection device includes a resilient member for biasing the syringe and needle inwardly of the housing.

The drive element may move the needle of the syringe out of the opening against the bias of the resilient member.

Preferably, the housing includes a release portion which interacts with the engagement to release drive to the syringe.

In this way, engagement may be released by virtue of the relative position of the syringe in the housing.

Preferably, the release portion is located in the housing at a predetermined position and the engagement includes a trigger which is operated by the release portion to release drive to the syringe upon reaching the predetermined position.

In this way, the needle is assuredly extended by the right amount.

Preferably, the engagement includes a resilient latch and the release portion includes at least a recess in a wall of the housing allowing deflection of the resilient latch to release the drive to the syringe.

Hence, the wall of the housing may maintain the resilient latch in a position of engagement until it reaches a recess or even an opening in the wall.

Preferably, the at least a recess engages the resilient latch so as to prevent further relative movement of the syringe body in the housing.

Thus, when the resilient latch moves into the recess or opening it may then engage with the recess or opening so as to fix the relative position between the syringe and the housing.

As described above, the drive coupling may include a fluid chamber defined between first and second relatively movable walls, the first wall being part of a piston and the resilient latch operating on the piston.

By engaging with either the dispensing piston or a secondary piston (forming with the dispensing piston a fluid chamber), the relative position between the dispensing piston and the syringe body can be fixed, such that any drive applied to the drive coupling or dispensing piston will result in movement of the syringe rather than the dispensing piston relative to the syringe.

The drive coupling may include a rigid element extending from the drive element, the engagement may include at least one protrusion on a surface of the rigid element and a latch fixed relative to the syringe body engaging the protrusion and the release portion may include a stop on the housing for engaging the latch wherein the rigid element moves the latch with the protrusion until the latch abuts the stop, whereupon the latch releases from the protrusion.

The latch may be deflected resiliently past the protrusion. However, alternatively, the latch may be hinged as a cantilever at a point between an end engaging protrusion and an opposite end wherein the stop deflects the opposite end so as to release engagement with the protrusion.

The latch may be hinged at the point at which it is attached to the syringe or alternatively to a part of the drive coupling mounted to the syringe with a fixed relative position to the needle.

The engagement may releasably connect the drive coupling to the syringe. Alternatively, the engagement may releasably connect a part of the drive coupling movable with the drive element to a part of the drive coupling to be mounted to the syringe in a fixed relative position to the needle.

BRIEF DESCRIPTION OF THE DRAWINGS

The invention will be more clearly understood from the following description, given by way of example only, with reference to the accompanying drawings, in which:

FIG. 4 illustrates schematically an injection device in which the drive coupling is incorporated into the syringe cartridge itself;

DETAILED DESCRIPTION

As will be apparent from the above, the present invention concerns injection devices and is based on driving the dispensing piston of a syringe with a drive coupling which can gradually reduce in length so as to ensure that the dispensing piston is moved fully along the length of the syringe and that the needle is held in its extended position by an appropriate force until that time.

Figure 2:
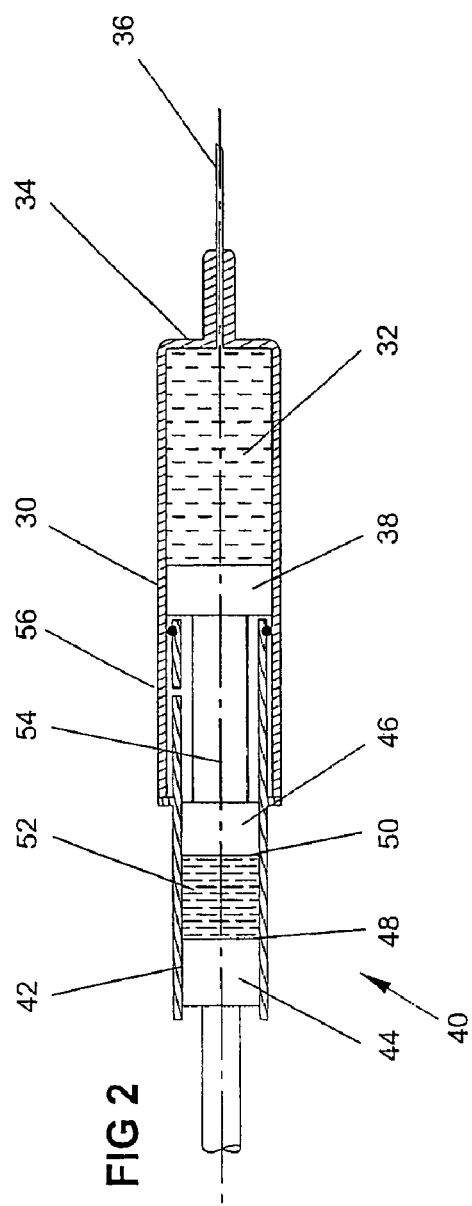
FIG. 2 illustrates a drive coupling according to the present invention.

FIG. 2 illustrates an embodiment of a suitable drive coupling.

The drive coupling is for use with a syringe 30, such as a standard syringe or cartridge, which includes a bore 32 extending from an end surface 34 within that bore and a needle 36 which communicates with the bore 32 through the end surface 34. A dispensing piston 38 is movable along the bore 32 towards the end surface 34. In particular, by moving the dispensing piston along the length of the syringe until it abuts the end surface 34, the entire contents of the syringe may be expelled through the syringe needle 36.

As illustrated, the drive coupling 40 includes a main body 42 which mates with the end of the syringe 30.

The main body 42 includes an elongate through passage along which a first piston 44 and a second piston 46 may move. The first piston 44 defines a first wall 48 facing a second wall 50 defined by the second piston 46.

The first wall 48 and second wall 50, together with the elongate passage 43, define a chamber 52 filled with fluid a material which is substantially incompressible, mobile under pressure and capable of extrusion. Materials such as powders, greases and soft solids may be used. However, in a preferred embodiment, a fluid is used such that chamber 52 will be described as a fluid chamber. This fluid is preferably liquid and substantially incompressible.

The first piston 44 and, hence, the first wall 48 may be driven by the drive element of an injection device. This is illustrated more clearly in FIG. 3.

As the first piston 44 is moved along the elongate passage 43, since the fluid in the fluid chamber 52 is substantially incompressible, the second wall 50 and, hence, the second piston 46, is also moved along the elongate passage.

For convenience of design, a spacing element 54 transfers drive from the second piston 46 to the dispensing piston 38 of the syringe 30.

Thus, the drive coupling 40 transfers movement to the dispensing piston 38.

At a predetermined position along the length of the passageway 43, a bleed orifice 56 is provided. Once the second wall 50 passes the bleed orifice 56, fluid is able to bleed from the fluid chamber 52 to outside the main body 42. As this fluid bleeds away, the volume of the fluid chamber 52 will be reduced and the distance between the first wall 48 and the second wall 50 will also be reduced.

The predetermined position of the bleed orifice 56 is chosen such that, with the main body 42 mated to the syringe 30 and having a fixed relative position, the second wall 50 will pass the bleed orifice 56 just before the dispensing piston 38 reaches the end surface 34.

It will be appreciated that, theoretically, the second wall 50 could open the bleed orifice 56 just as the dispensing piston 38 reaches the end surface 34. However, the present invention is based on a recognition that tolerances, particularly the compound effect of tolerances of different components, mean that such design cannot be guaranteed. Therefore, the second wall 50 exposes the bleed orifice 56 when the dispensing piston 38 is at a position proximate the end surface 34 so as to ensure that the bleed orifice 56 is open by the time the dispensing piston 38 abuts the end surface 34.

It will be appreciated that, even with the bleed orifice 56 open, some driving force will still be transmitted to the second piston 46 such that the dispensing piston 38 will be driven the final small distance to the end surface 34 to dispense the remaining contents of the syringe 30.

With the dispensing piston 38 abutting the end surface 34, the second piston 46 and second wall 50 will move no further. However, as fluid bleeds from the fluid chamber 52, the first wall 48 and first piston 44 will continue to move towards the end surface 34 until a return delatch mechanism is operated to retract the syringe 30 and needle 36 back into the housing of the injection device.

Figure 3:
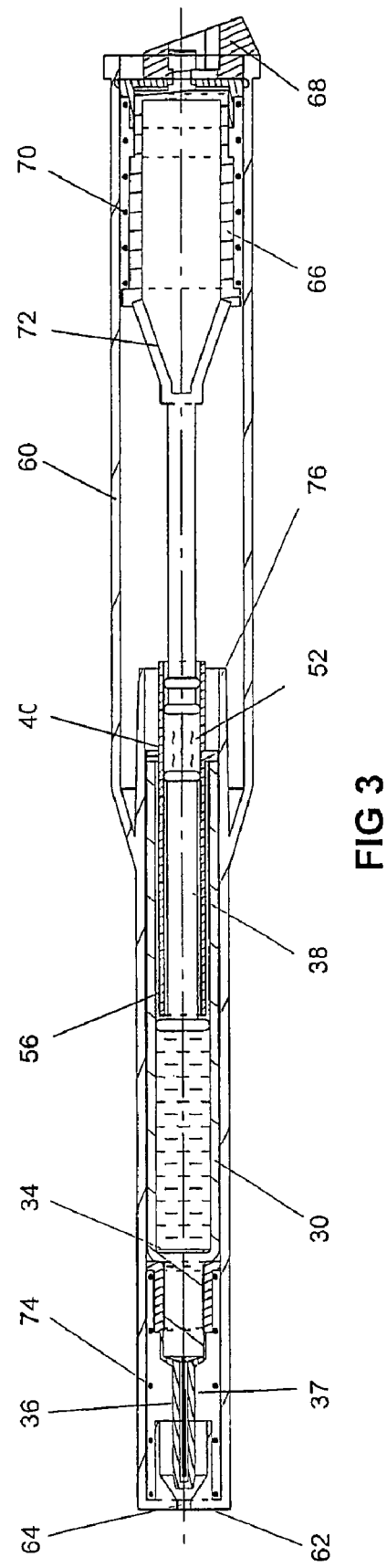
FIG. 3 illustrates the drive coupling of FIG. 2 incorporated into an injection device similar to that illustrated in FIG. 1.

The particular nature of the return delatch mechanism is not essential to the present invention and any suitable mechanism may be employed. Similarly, the drive element may be operated in any known manner, for instance using springs, gas pressure, manual operation, etc. Nevertheless, FIG. 3 illustrates an injection device similar to that of FIG. 1 incorporating a drive coupling like that of FIG. 2.

The syringe 30 is contained within the housing 60 of the injection device. The housing 60 has a first end 62 in which an opening 64 is formed.

In use, a drive element 66 is released using a button 68 and a drive spring moves the drive element 66 towards the end 62.

Figure 1:
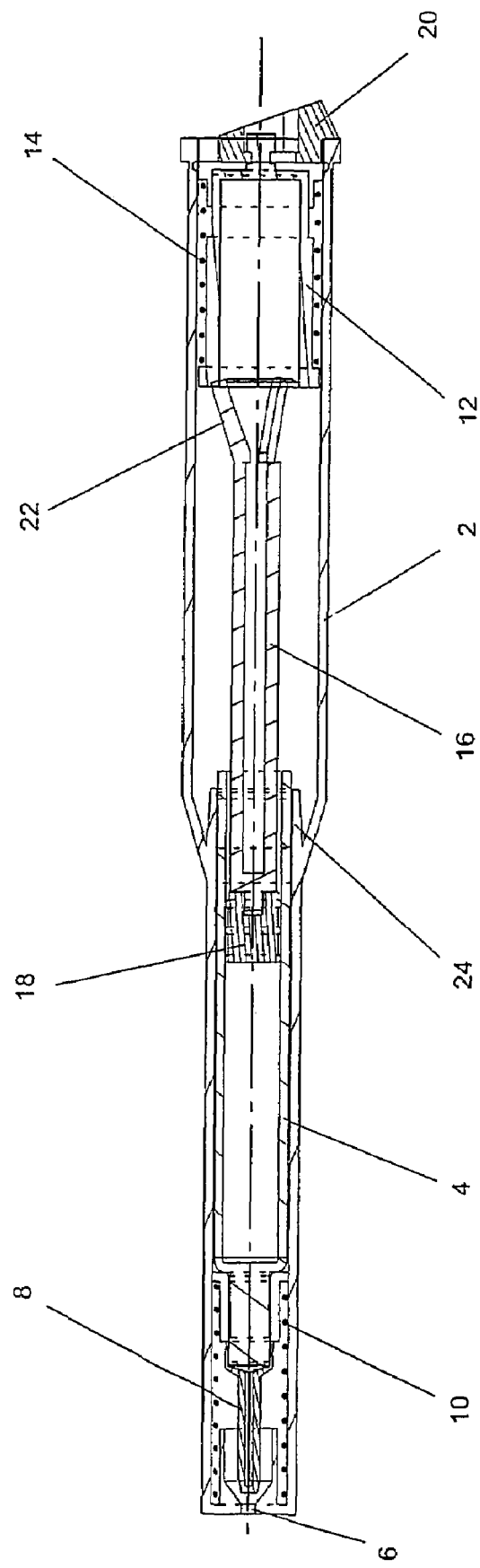
FIG. 1 illustrates a known construction for an injection device.

As with the device of FIG. 1, a latch 72 in the form of resiliently deflectable arms, is provided between the drive coupling 40 and the drive element 66. By means of the latch arrangement 72 and the drive coupling 40, the syringe 30 is driven towards the end 62 against the bias of the return spring 74 so that the needle 36 extends out of the device.

In particular, a rubber seal 37 is provided over the needle 36 so as to maintain sterility. The rubber seal 37 abuts the surround of opening 64, the needle pierces the rubber seal 37 and then the rubber seal concertinas as the syringe moves forward. It will be appreciated that the rubber seal provides some resistance to movement of the syringe and that the coupling 40 needs to overcome the resistance.

As explained above, the drive coupling 40 then enables the dispensing piston 38 to be moved all the way to the end surface 34 so as to expel the entire contents of the syringe 30. By means of the drive coupling, in this embodiment using the fluid chamber 52 and bleed orifice 56, the drive coupling reduces in length under the force of the drive element allowing the drive coupling to move within the drive element 66 and the return spring 74 to 66 and drive spring 70 until the collar 76 deflects the arms of the latch mechanism 72 retract the syringe 30 and needle 36.

Thus, the drive coupling acts as a controlled collapsing element which remains rigid during the majority of the dispensing piston travel. When the dispensing piston 38 nears the end surface 34 of the syringe, the controlled collapsing element collapses in such a way that it can continue to transfer force (and motion) from the drive mechanism to the dispensing piston while it collapses. This enables the dispensing piston to be pushed to the end of the syringe (expelling all of the contents) before the delatching mechanism 72 has travelled far enough to reach the trigger point. After the dispensing piston 38 has reached the end of the syringe, the controlled collapsing element 40 continues to collapse under the force of the drive mechanism. This enables the delatching mechanism 72 to continue to move forwards until it reaches the trigger point 76, when it will delatch and allow needle retraction to occur. In other words, the drive coupling reduces in length or the controlled collapsing element collapses over a finite and controllable period of time, enabling the continued forward travel of the delatch mechanism after the dispensing piston has reached the end of the syringe.

It will be appreciated that fluid escaping from the bleed orifice will have to be captured. Although not illustrated, this may be achieved by any suitable means, for instance wicking it on to a suitable absorbent material (held within the device) or trapping it between seals in the device.

Although the preferred embodiment as described above allows the drive coupling to reduce in length only when the dispensing piston approaches the end surface of the syringe, where the drive coupling reduces in length at a rate which is relatively slow with respect to movement of the dispensing piston 38, it is possible for the drive coupling to gradually reduce in length throughout the entire dispensing operation. As a modification of the embodiment described above, one or more bleed orifices along the length of the passageway 43 may achieve this or, alternatively, bleed orifices through one or both of the first piston 44 and second piston 46. Indeed, any other suitable fluid damped collapsing arrangement could be used.

The description given above principally concerns the use of a drive coupling with standard unmodified known syringes or cartridges. However, by providing syringes or cartridges intended specifically for this use, a drive coupling according to the present invention may be implemented as part of the syringe itself. This is illustrated schematically in FIG. 4(a).

Rather than provide a separate body and passageway for the fluid chamber, as illustrated, a fluid chamber 80 is provided within the bore 82 of the syringe 84 itself. The fluid chamber 80 is formed between a first wall 86 and a second wall 88. However, although the first wall 86 is formed on a first piston 90, the second wall 88 is formed on the dispensing piston 92. Of course, it would also be possible to provide a second piston in the bore 82 for driving the dispensing piston 92.

In a manner equivalent to that described for the embodiment of FIG. 3, a bleed hole 94 is provided through the wall of the syringe 84. Thus, in the same way, the bleed orifice 94 is positioned such that it connects with the fluid chamber 80 just before the dispensing piston 92 contacts the end surface 96 of the syringe 84. After the dispensing piston 92 contacts the end surface 96 bleeding of fluid from the fluid chamber 80 will allow the first piston 90 to continue moving along the syringe until an appropriate retract mechanism is operated.

For the illustrated embodiment, it will be appreciated that the moment at which the bleed orifice 94 opens to the fluid chamber 80 is dependent only on tolerances of the dispensing piston 92 and the position of the bleed orifice 94. Following on from this, it is possible to make further use of the bleed orifice 94.

In particular, by providing a bleed orifice 94 which is elongate in the direction of travel of the dispensing piston 92 or by providing an array of orifices extending in that direction, it means that, as the dispensing piston 92 moves towards the end surface 96, the cross-sectional area available for bleeding increases. Hence, increased bleeding can be obtained as the dispensing piston 92 reaches the end surface 96. This may enhance or decrease the time needed to actuate the retraction mechanism. Indeed, by providing a large bleed cross-sectional area at exactly the position where the dispensing piston 92 reaches the end surface 96, it is possible to empty fluid from the fluid chamber 80 at a sufficient rate to allow the return spring 98 to retract the syringe 84 and needle 100. Hence, the fluid chamber 80 and bleed orifice 94 effectively forms the return mechanism with the return spring 98.

FIG. 4(*b*) illustrates a possible triangular cross-section for the bleed orifice 94.

Figure 5B:
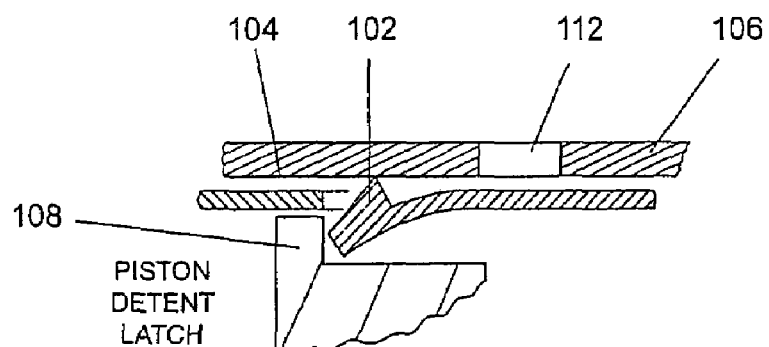
FIG. 5 illustrates an embodiment providing direct drive to the syringe.
Figure 5A:
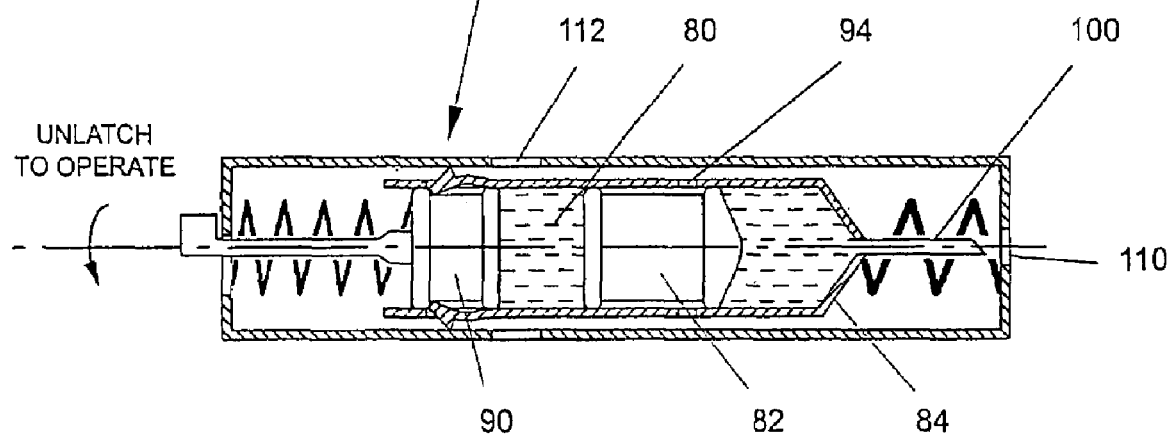

FIG. 5(*a*) illustrates schematically a similar device having a latch mechanism illustrated more clearly in FIG. 5(*b*), the outer wall of the syringe 84 includes latches 102 which are deflected inwardly by the inner surface 104 of the housing 106 of the injection device. As a result, the first piston 90, for instance by means of a flange 108 engages the inwardly deflected latch 102. Thus, when the first piston 90 is moved to operate the syringe 84, it is not able to move relative to the syringe 84 by sliding within the bore 82. Instead, it pushes upon the latches 102 and directly moves the syringe 84 so as to move the needle 100 through the opening 110 in the injection device.

Openings 112 are provided in the housing 106 at radial positions corresponding to the positions of the latches 102. Thus, when the first piston 90 moves the syringe 84 forward to the point where the latches 102 reach the openings 112, the latches 102 move outwardly into the openings 112, thereby releasing the first piston 90. In this embodiment, the latches 102 also prevent further forward movement of the syringe 84 itself. Subsequent movement of the first piston 90 will cause compression of the fluid in the fluid chamber 80 and movement of the dispensing piston 92 in the manner described above.

By virtue of the sloped profile of the latches 102, when the syringe 84 is retracted, the latches are once again deflected inwardly of the housing 106 out of the openings 112, thereby allowing movement of the syringe 84.

Figure 6:
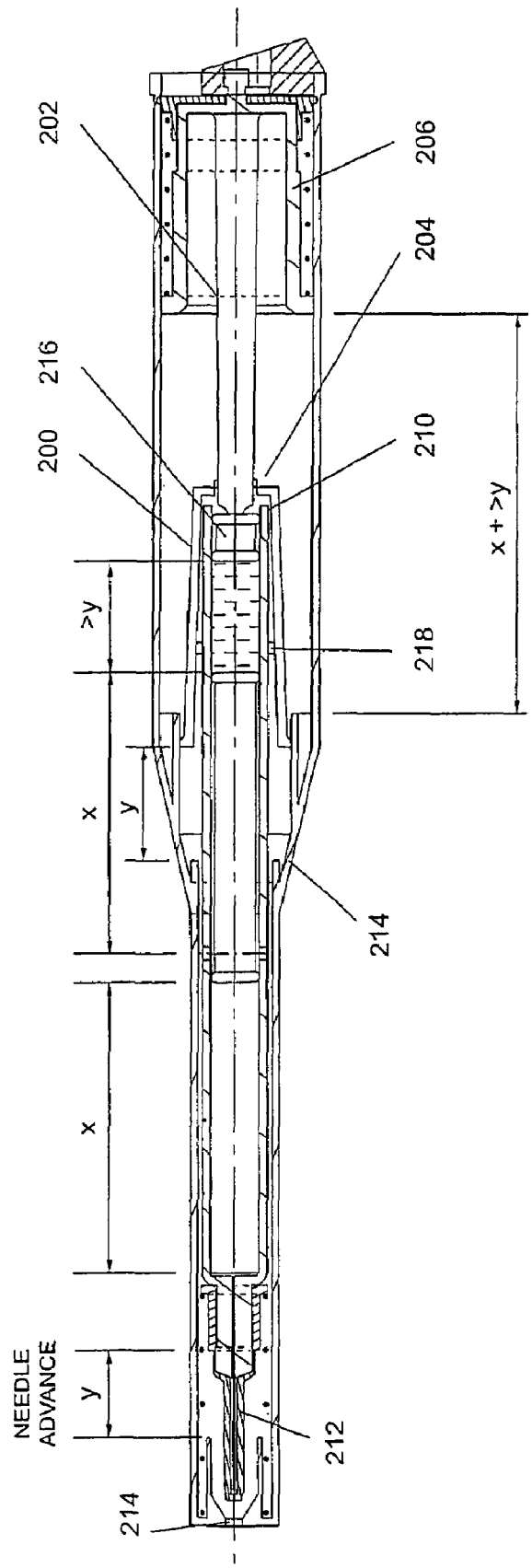
FIG. 6 illustrates an alternative embodiment providing direct drive to the syringe.

FIG. 6 illustrates an embodiment similar to that of FIG. 4(*a*) but incorporating an alternative to the latch of FIG. 5(*b*).

As illustrated two or more latch levers 200 extend forwardly from a rear portion of a drive coupling 202. They engage with the drive coupling by means of a detent arrangement. As illustrated, the drive coupling includes one or more protrusions 204.

In use, when the drive element 206 starts to travel along the device, the detent arrangement, for instance the protrusions 204, engage the ends of the levers 200. The levers in turn push on the housing 210 of the syringe, for example by the ends of the levers 200 abutting the end of the syringe body. Hence, the syringe is assuredly pushed forward until the needle 212 extends from the opening 214.

When the opposite ends of the levers 200 reach abutments 214 in the housing, further movement of the drive element 206 overcomes the detent such that the piston is then driven.

This may be achieved by forming the ends of the levers 200 as a single resilient ring which merely deflects around the protrusions 204. However, as illustrated, the levers 200 are actually provided with hinges 218, such that the inwardly sloping walls of the housing cause the levers to disengage from the protrusions 204. The hinges may attach the levers 200 to the syringe body and indeed the levers, hinges and syringe body may be formed integrally as a single unit.

It will be appreciated that other detent or latch arrangements are also possible, for instance with the ends of the levers 200 engaging in recesses in the drive coupling 202.

It is also possible to make use of a resilient o-ring to provide an inward bias to the levers 200.

This general construction ensures that the syringe is fully extended from the injection device before any fluid is expelled from the syringe. It will be appreciated that equivalent mechanisms may be used in conjunction with the other embodiments, for instance providing latches in the main body of the drive coupling. Indeed, this construction could also be used in other arrangements without the arrangement of the drive coupling which reduces in length.

The present invention need not be implemented only with a collapsible fluid chamber. Any other suitable collapsible arrangement may also be used.

Figure 7:
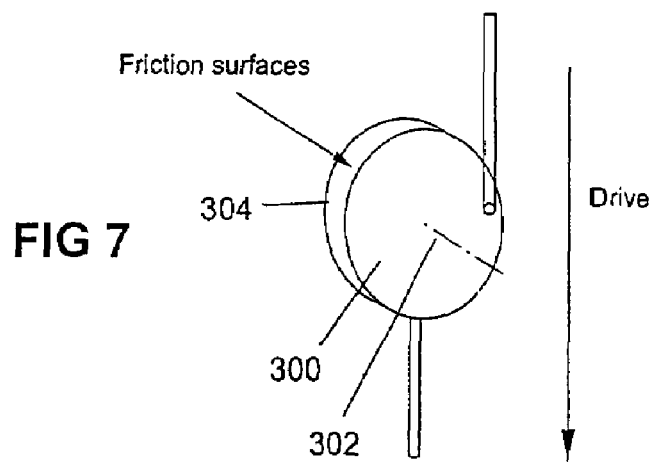
FIG. 7 illustrates schematically a friction plate embodiment.

FIG. 7 illustrates schematically an alternative arrangement. A drive plate 300 is rotatable about an axis 302 and includes a frictional surface mating with the frictional surface of a driven plate 304. As illustrated, the driven plate 304 is to be connected to a dispensing piston of a syringe, whereas the drive plate 300 is moved by a drive element of an injection device.

As illustrated, the drive element connects to the drive plate 300 at a position offset from the rotational axis 302 so as to form a crank arrangement.

In use, the drive element applies a tangential force to the drive plate 300, but, because of the frictional resistance between the frictional surfaces of the drive plate 300 and the driven plate 304, the drive plate 300 does not rotate about its axis 302. Instead, the entire arrangement is moved in the direction of the force so that the driven plate 304 moves the dispensing piston of the syringe. Once the dispensing piston reaches the end of its travel and the driven plate 304 can move no further, the frictional resistance between the plate 304 is overcome and the drive plate 30Q starts to rotate about its axis 302. Because of the offset connection to the drive plate 300, this allows the drive element of the ejection device to move further and the retraction mechanism to be operated. The frictional resistance between the two plates will maintain the force on the dispensing piston of the syringe.

Figure 8:
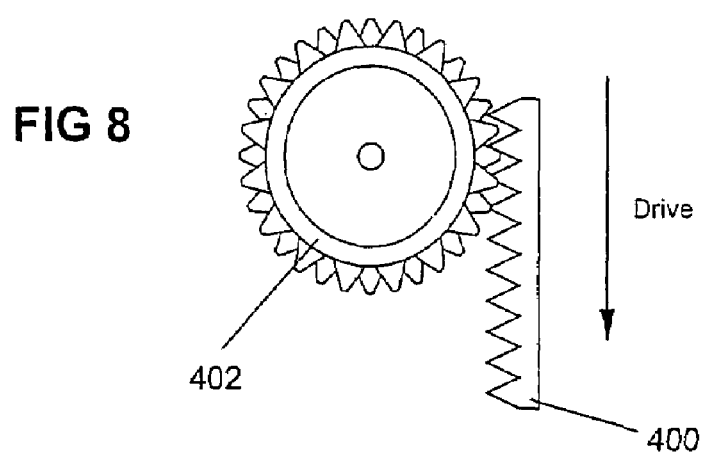
FIG. 8 illustrates schematically a rack and pinion embodiment.

FIG. 8 illustrates schematically an embodiment in which the drive coupling includes one component having a rack gear 400 and another component rotatably supporting a pinion gear 402. The pinion gear is provided with some means to resist rotation, for instance by means of friction contact.

When the drive coupling is used to move the dispensing piston of a syringe, the pinion gear 402 will resist rotation and, hence, the drive coupling will maintain its length. However, once the dispensing piston reaches the end of its travel in the syringe, the drive coupling will come under a compressive load and the pinion gear 402 will be rotated by the rack gear 400. In this way, the length of the drive coupling will gradually be reduced whilst the frictional resistance of the pinion gear 402 will maintain the force on the dispensing piston of the syringe. Hence, the drive element will continue to move until an appropriate retract mechanism is operated.

Figure 9:
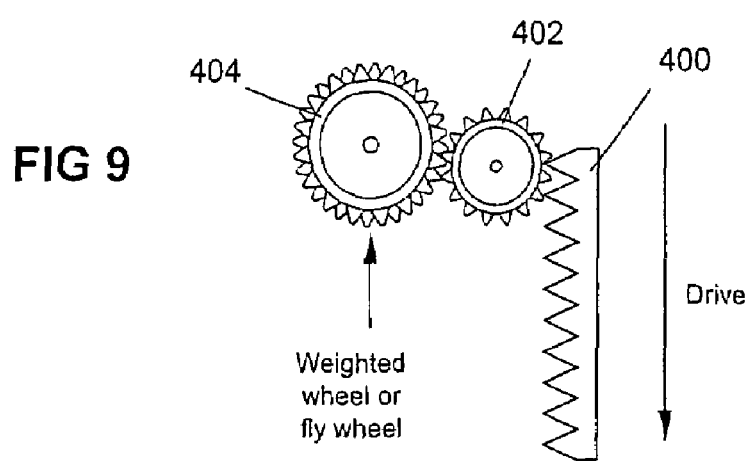
FIG. 9 illustrates schematically a rack and pinion construction using a fly wheel.
Figure 10:
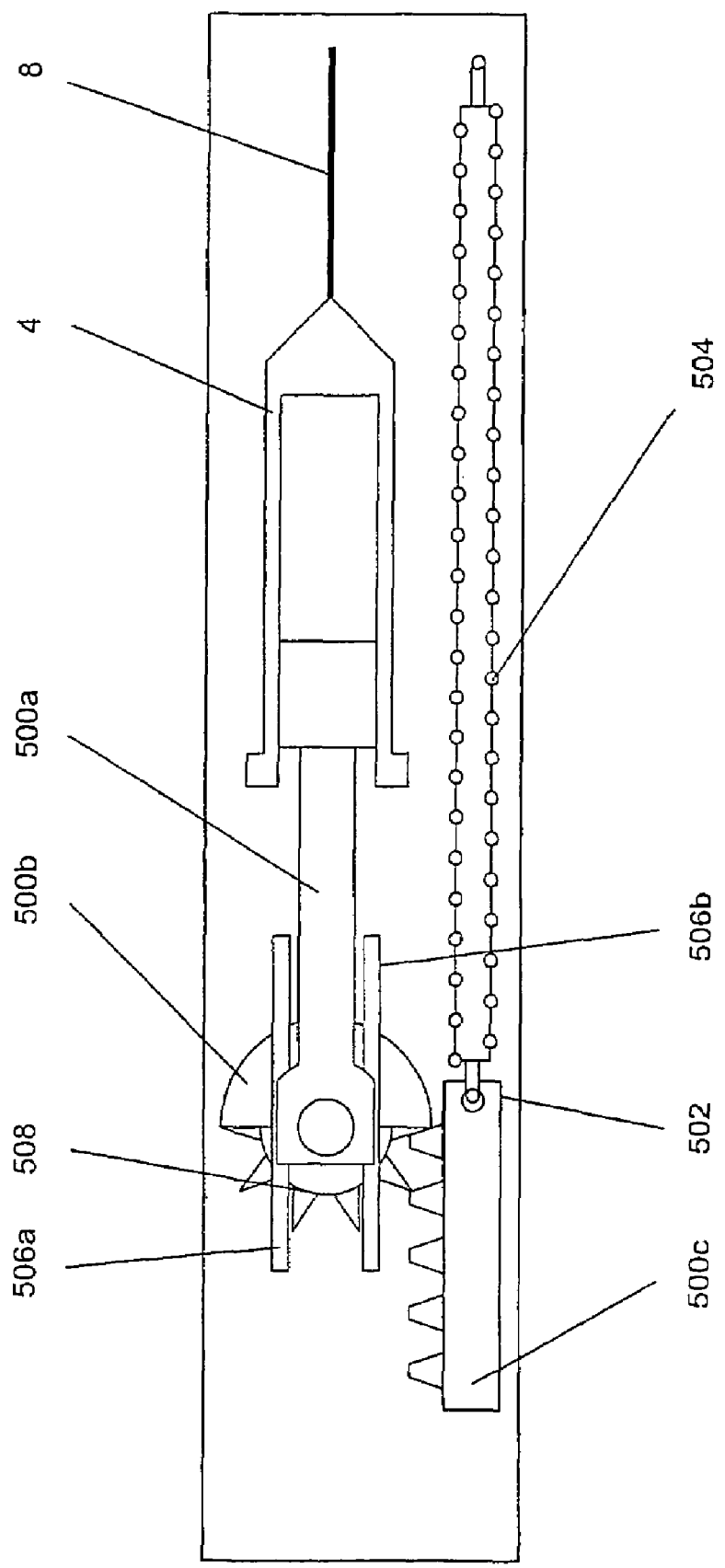
FIGS. 10 to 15 illustrate an alternative embodiment of a drive coupling of the present invention.

FIG. 9 illustrates a development of the embodiment of FIG. 8 in which the frictional resistance to the pinion gear 402 is replaced by the inertial resistance of a fly wheel 404 or the like.

It should be appreciated that the frictional and inertial arrangements of FIGS. 7 to 9 could also be replaced with viscous dampers.

FIGS. 10 to 15 illustrate schematically components of a further embodiment of the present invention. For simplicity of understanding the functioning of the device, the Figures illustrate only those components of importance to the difference between this embodiment and those described above. For instance, the housing, retraction spring and release mechanism are not illustrated.

The drive coupling in this embodiment comprises three components, namely a connection member 500*a*, a pinion gear 500*b* and a rack 500*c*. The drive element can be considered to be the end portion 502 of the rack 500*c*. A drive spring 504 is connected to the end portion or drive element 502 so as to bias the drive element 502, drive coupling 500*a, b* and *c* and the syringe 4 towards one end of the housing as described previously above.

The pinion 500*b* is rotatably mounted on the end of the member 100*a*. Teeth of the pinion 500*a* engage with the teeth of the rack 500*c*. Within the housing, means are provided to prevent the pinion 500*b* from rotating. Thus, in the illustrated embodiment, a pair of longitudinally extending rails 506*a* and 506*b* extend either side of an axially extending protrusion 508 on the pinion 500*b*. Of course, it will be appreciated that only one such rail could be used or indeed, it could be replaced with a channel section.

Figure 11:
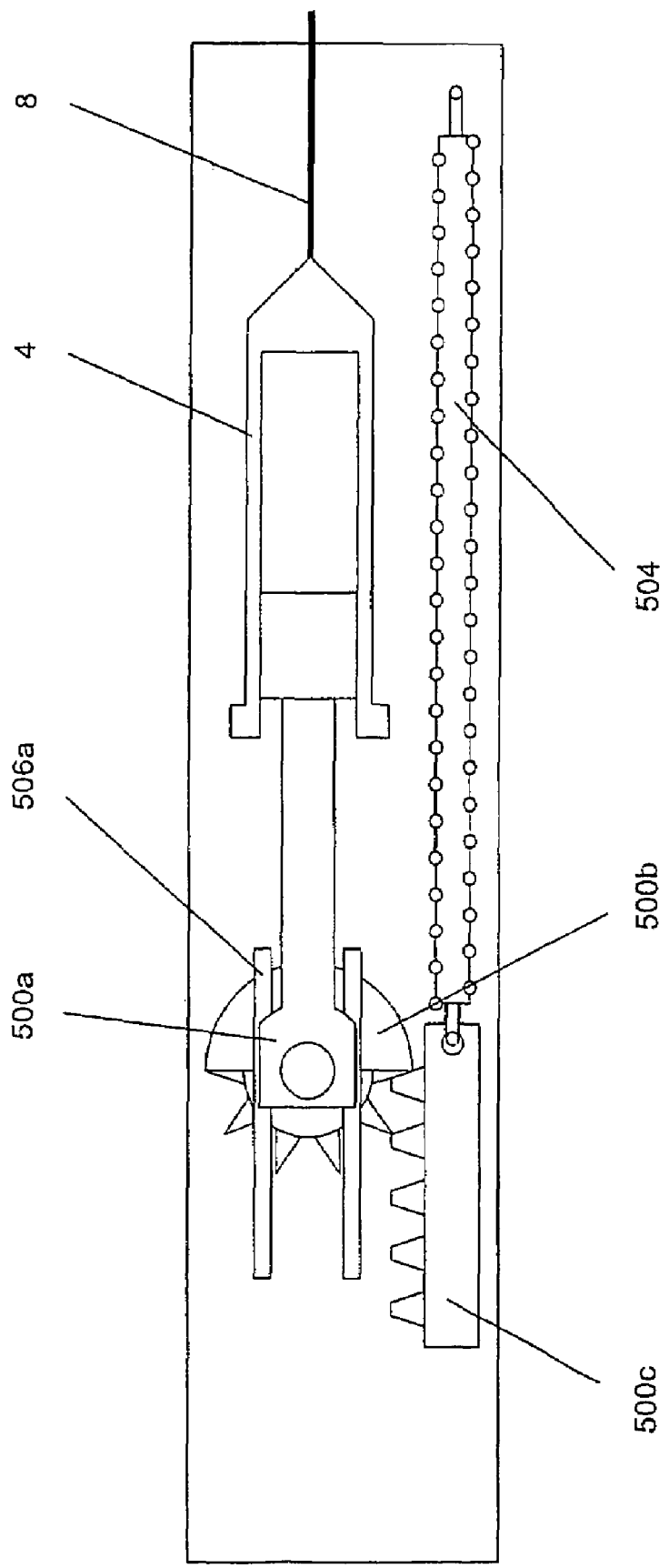

In use, the drive spring 504 acts to move the rack 500*c* in a direction to eject the needle 8 of the syringe 4. The teeth of the rack 500*c* act on the pinion 500*b*. However, since the pinion 500*b* is restrained from rotating, the shaft 500*a* is moved longitudinally so as to move the syringe 4 and extend or eject the needle S. This is illustrated in FIG. 11.

Figure 12:
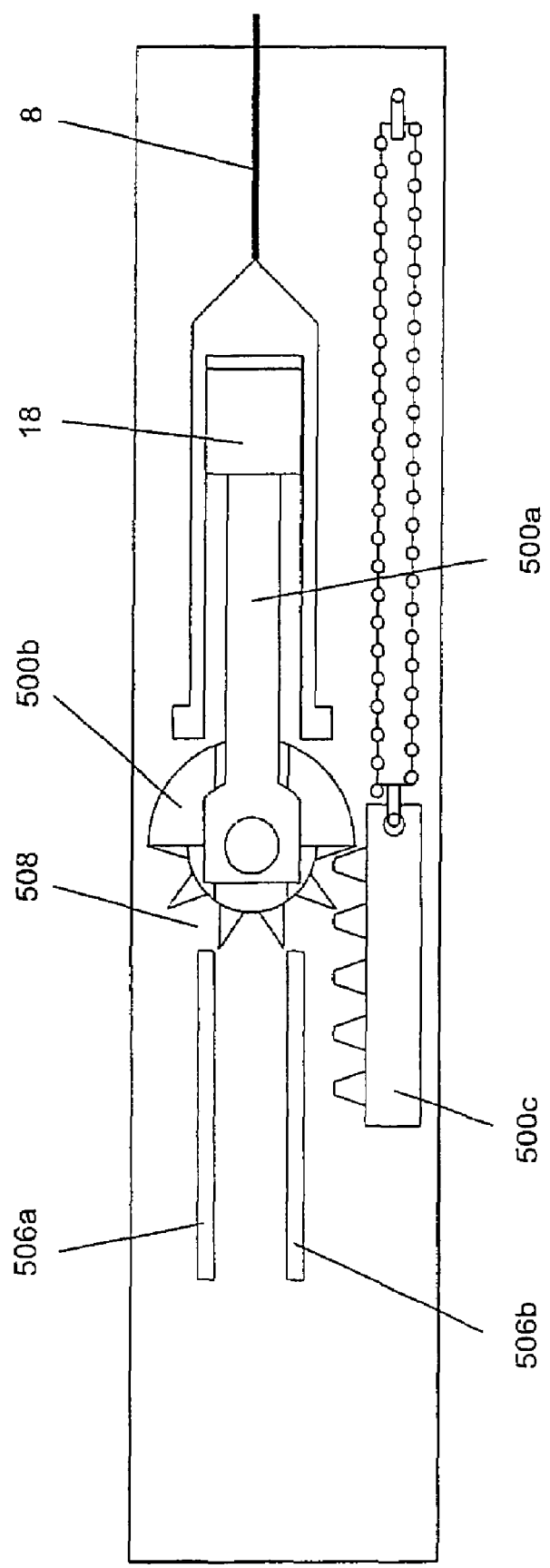
Figure 13:
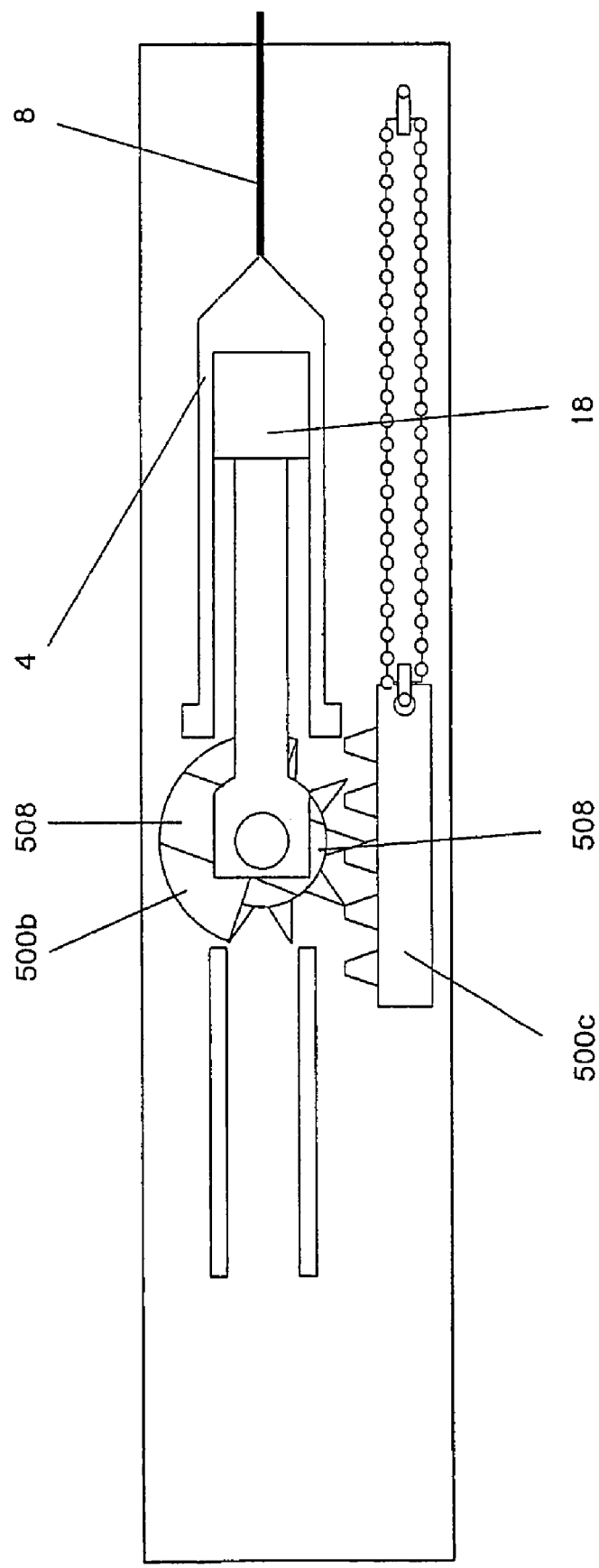

The means for preventing rotation of the pinion 500*b*, in the illustrated embodiment, the rails 506*a* and 506*b* only extend for a predetermined length. In particular, the components are arranged such that just before the dispensing piston 18 reaches the end surface of the syringe 4 the axial protrusion 508 moves beyond the end of the rails 506*a* and 506*b* as illustrated in FIG. 12. At this point, further movement of the rack 500*c* will rotate the pinion gear 500*b* rather than move the member 500*a*. According to this embodiment of the present invention, some form of resistance, preferably in the form of damping is introduced to rotation of the pinion 500*b* with respect to the member 500*a*. In this way, the member 500*a* will continue to move the dispensing piston 18 towards the end surface of the syringe 4 whilst the rack 500*c* continues to move. This is illustrated in FIG. 13. The drive coupling 500*a, b, c* thus gradually reduces in length whilst the dispensing piston 18 is maintained at the end surface of the syringe 4.

A retract mechanism could be provided which is dependent on the position of the rack 500*c*. If the components are arranged such that the retract mechanism is only triggered once the rack 500*c* has reached a position in which it is ensured the dispensing piston 18 has reached the end surface of the syringe 4, then retraction of the syringe 4 will only occur after the entire contents of the syringe has been expelled.

Figure 14:
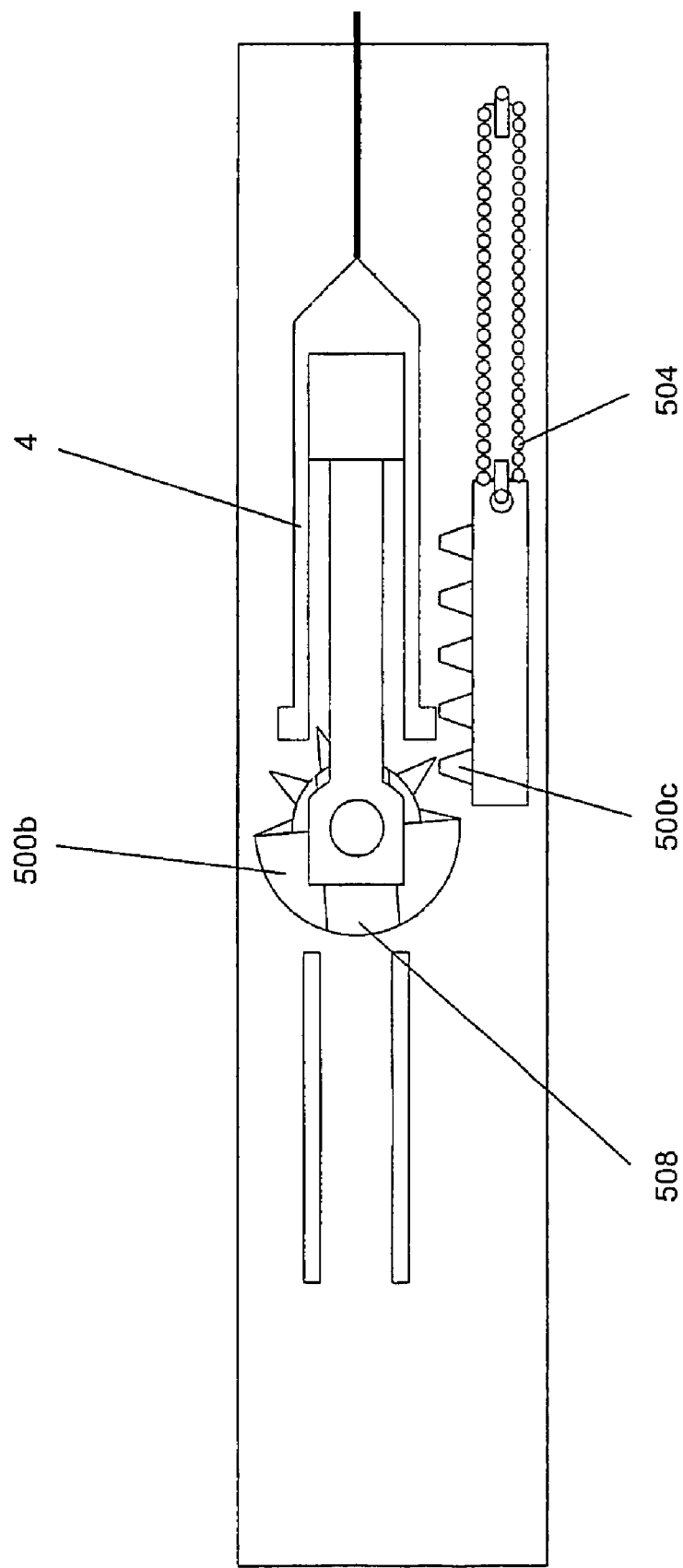

According to the illustrated embodiment, however, the rack 500*c* and pinion 500*b* themselves provide the retract mechanism. In particular, as illustrated in FIG. 14, the rack 500*c* continues to move, until its last tooth disengages with the pinion 500*b*. At this point, the pinion 500*b*, member 500*a* and syringe 4 are released such that a retract spring can retract the syringe 4 and needle 8 inwardly of the device.

Figure 15:
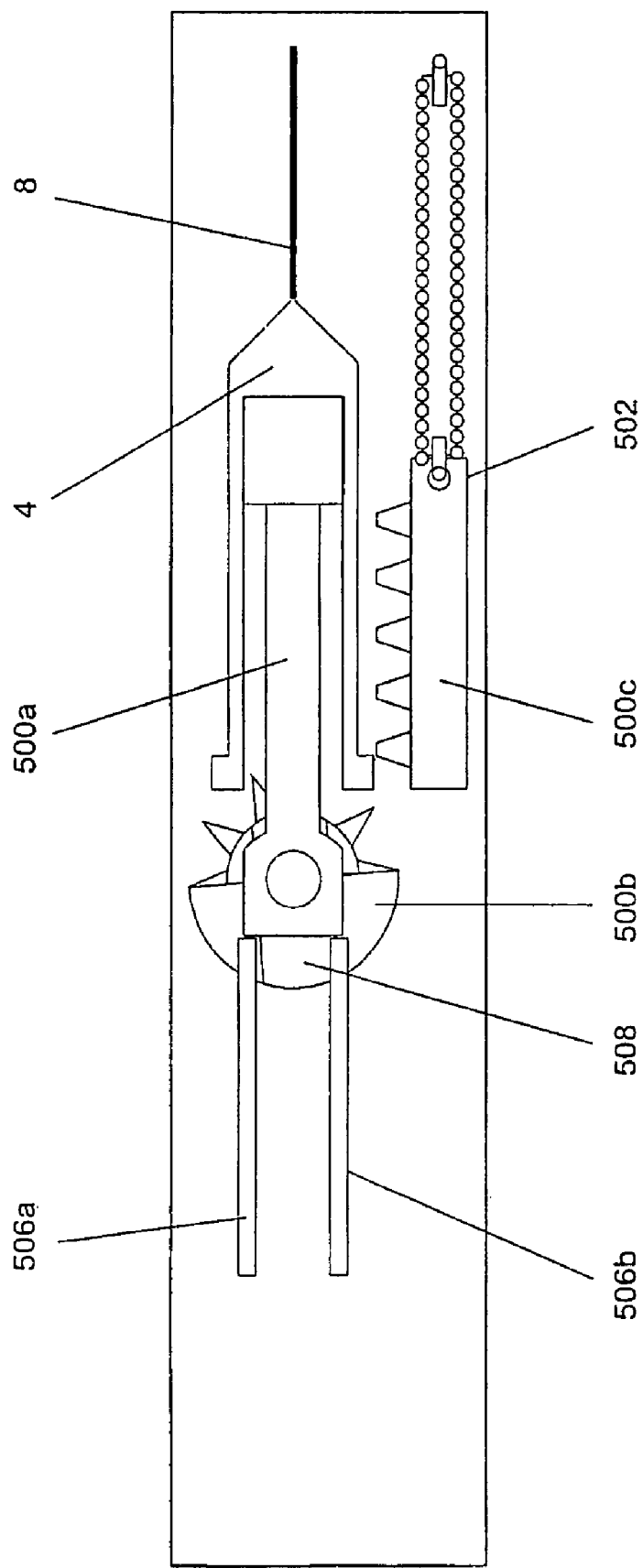
Figure 16:
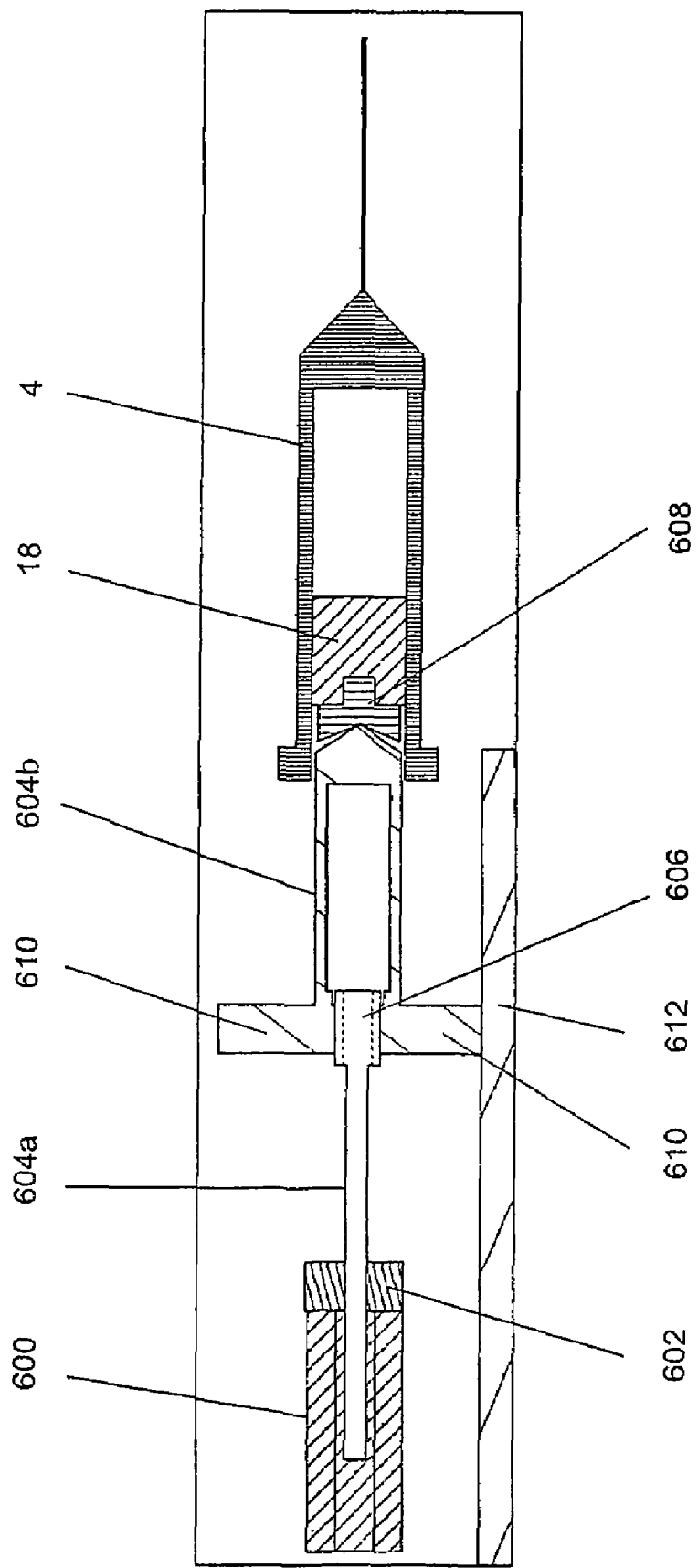
FIGS. 16 to 21 illustrate schematically another embodiment of a drive coupling of the present invention.

In the illustrated embodiment, the components, in particular the pinion 500*b*, are arranged such that, during travel of the rack 500*c*, the pinion 500*b* is turned through 180 degrees. In this way, the axial protrusion 508 may once again pass through the rails 506*a* and 506*b*. However, as illustrated in FIG. 15, since the dispensing piston 18 has moved within the syringe 4, it may not be necessary for the pinion 500*b* to move back that far in order to retract the needle 8.

FIG. 16 to 21 illustrate yet another embodiment of the present invention.

In this embodiment, as with others described above, a drive spring 600 acts on a drive element 602 so as to move a drive coupling. The drive coupling in this embodiment includes a non rotatable component 604*a* engaging by means of a thread with a rotatable component 604*b*. In the illustrated embodiment, the rotatable component 604*b* is generally hollow in cross section and includes a female thread for receiving a male thread of a threaded portion 606 on the end of the non rotatable component 604*a*. A bearing 608 is provided between the end of the rotatable portion 604*b* and the dispensing piston 18 of the syringe 4. In this way, the rotatable portion 604*b* is able to rotate relative to the non rotatable portion 604*a* such that, by means of the male and female threads, the non rotatable portion 604*a* and the rotatable portion 604*b* move longitudinally relative to one another.

Along a predetermined extent of the housing of the injection device, means are provided to prevent the rotatable portion 604*b* from rotating. As illustrated, the rotatable portion 604*b* includes at least one laterally extending arm 610 which engages with a longitudinally extending rib 612 having a predetermined length.

Figure 17:
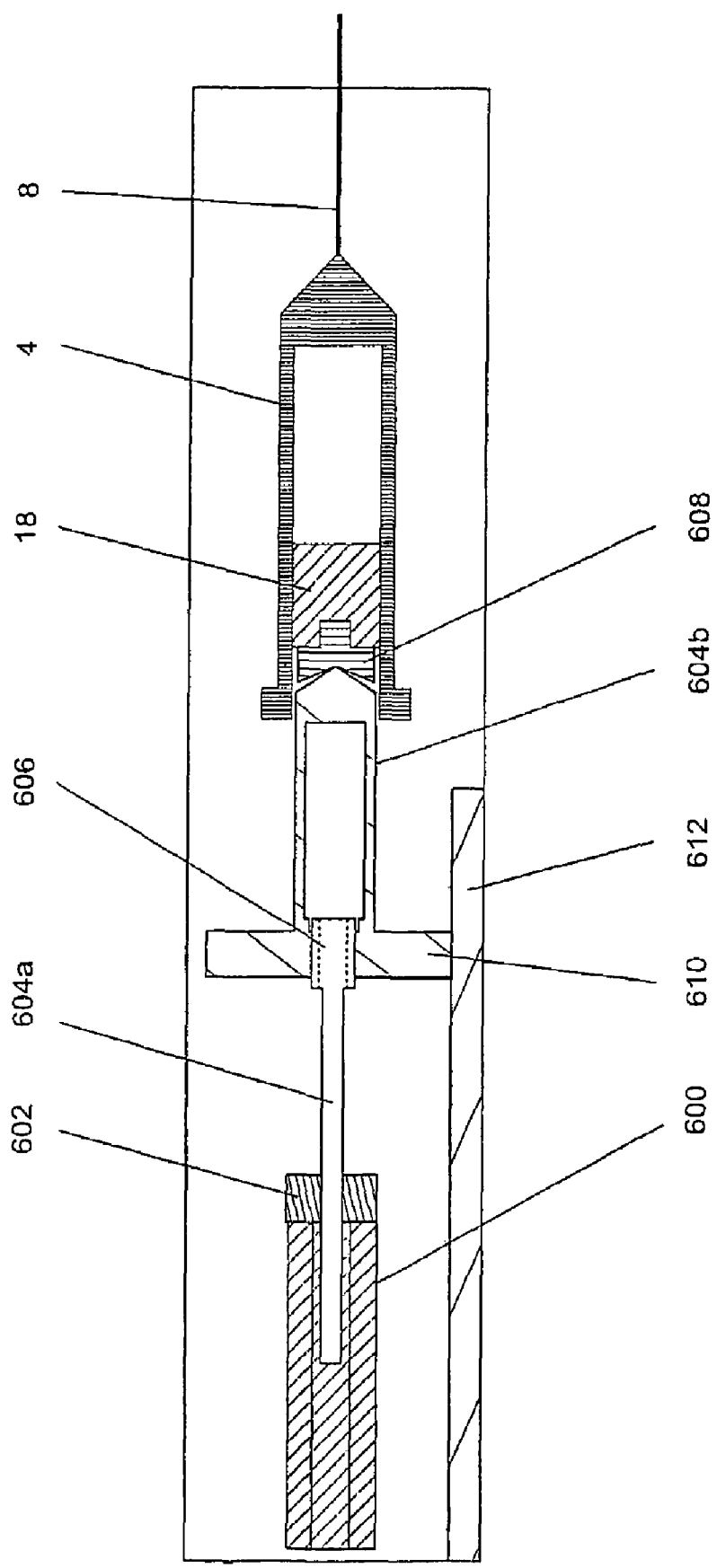

In use, when the drive spring 600 expands, the drive element 602 and drive coupling 604*a*, 604*b* move longitudinally so as to project the needle 8 of the syringe 4 out of the housing. This is illustrated in FIG. 17.

By virtue of engagement of the arms 610 with the ribs 612, the rotatable portion 604*b* is not able to rotate relative to the non rotatable portion 604*a* such that the drive coupling 604*a*, 604*b* maintains a constant length.

Figure 18:
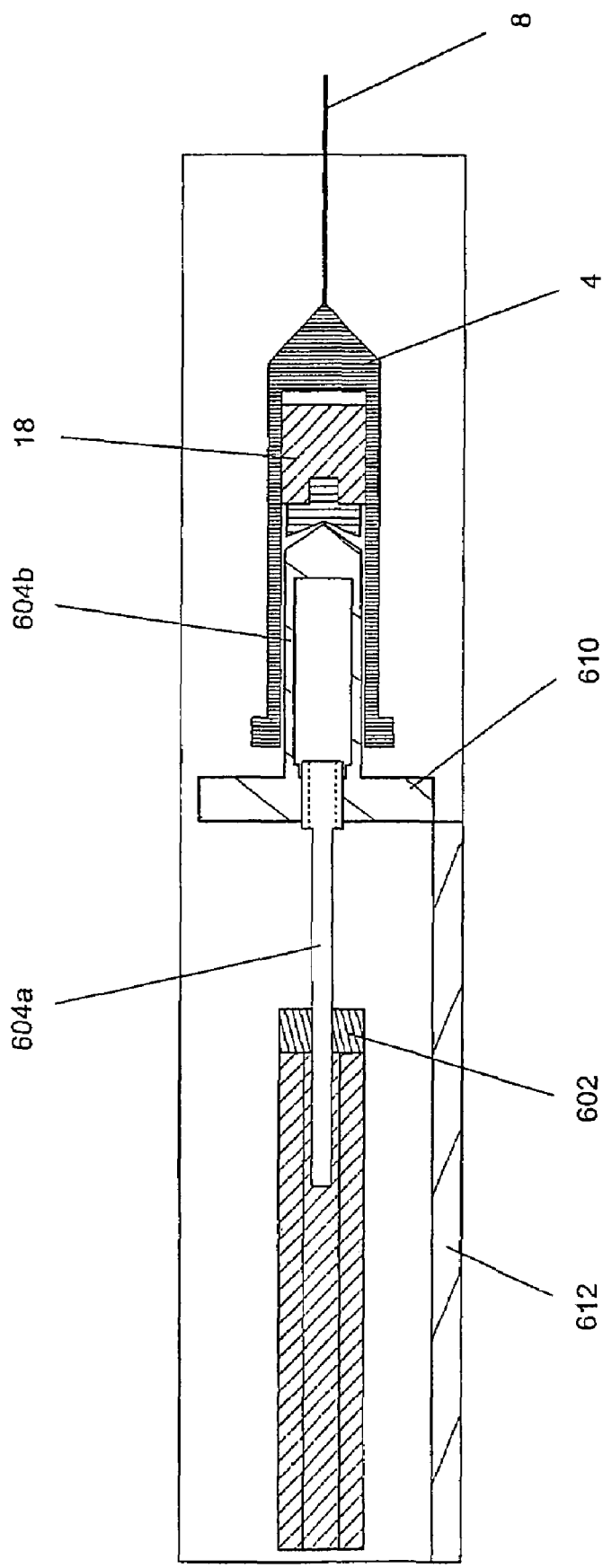
Figure 19:
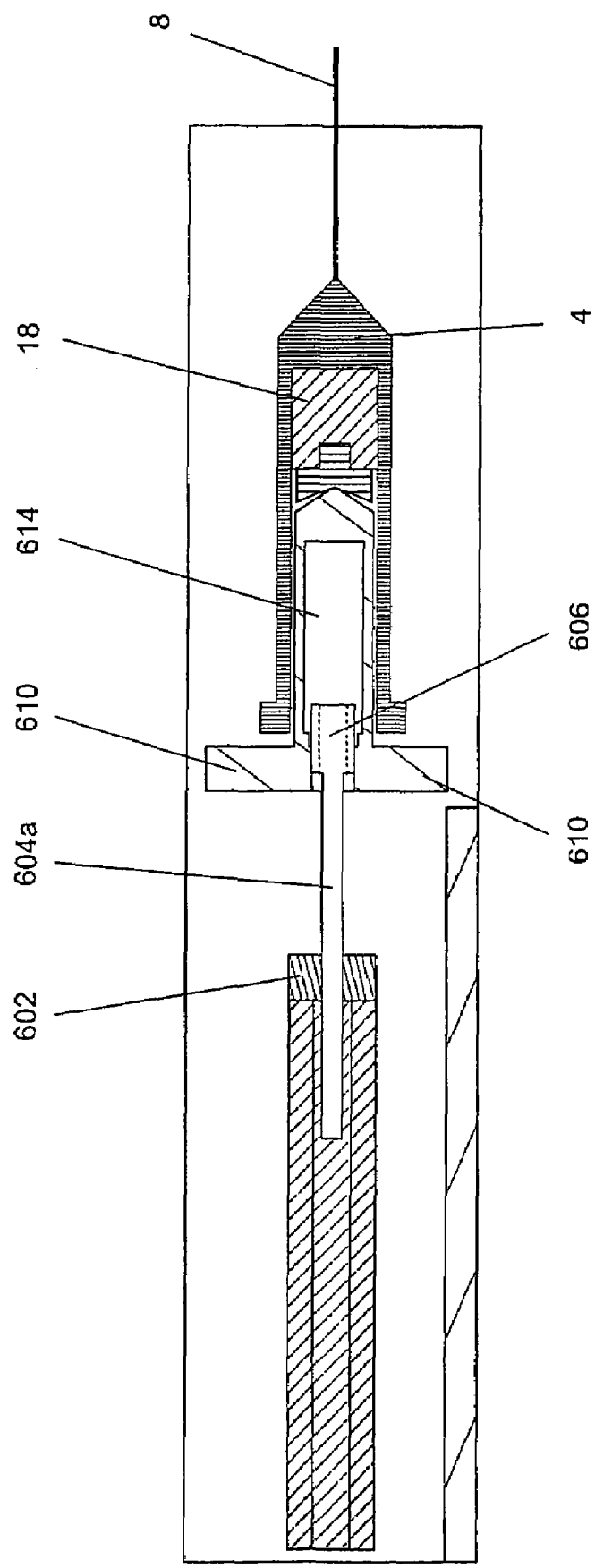

Further expansion of the drive spring 600 causes the drive coupling 604*a*, 604*b* to move the dispensing piston 18 within the bore of the syringe 4 so as to expel the contents of the syringe 4 through the needle 8. However, as illustrated in FIG. 18, the extent of the rib 612 is such that the lateral arm 610 moves to a position beyond the end of the rib 612 just before the dispensing piston 18 reaches the end surface of the needle 4. At this time, the rotatable portion 604*b* is able to rotate relative to the non rotatable portion 604*a*. Hence, as illustrated in FIG. 19, the threaded portion 606 moves inwardly of the rotatable portion 604*a*. By providing some resistance to movement, preferably in the form of damping, the rotatable portion 604*a* is still moved longitudinally so as to move the dispensing piston 18 to the end face of the syringe 4. Hence, the drive coupling 604*a*, 604*b* gradually reduces in length whilst the dispensing piston 18 is maintained at the end surface.

In a preferred embodiment, the arm 610 is intended to spin against the resistance of air. It may take the form of a simple flap or a maybe part of a turbine or propeller cross section. In the illustrated embodiment, at least a pair of flaps are provided.

The release mechanism may be dependent on the position of the drive element 602 and/or non rotatable component 604*a*. In particular, the syringe 4 and needle 8 may be retracted when the drive element 602 and non rotatable portion 604a reach a predetermined position in which it is certain that the dispensing piston 18 will have reached the end surface of the needle 4.

In the illustrated embodiment, the drive coupling 604a, 604b itself forms part of the retract mechanism.

As illustrated, the rotatable portion 604b defines an internal hollow space 614 which is not threaded and which is larger that the outer cross section of the threaded portion 606.

Figure 20:
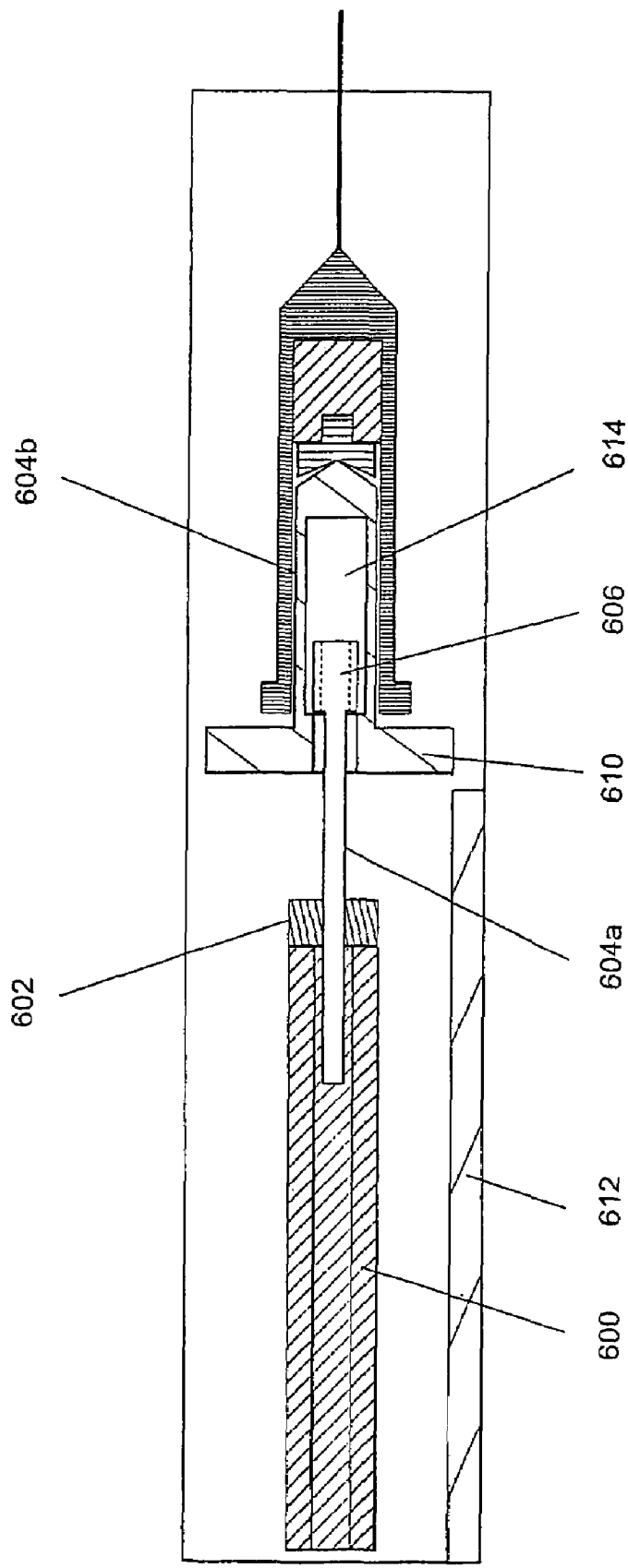
Figure 21:
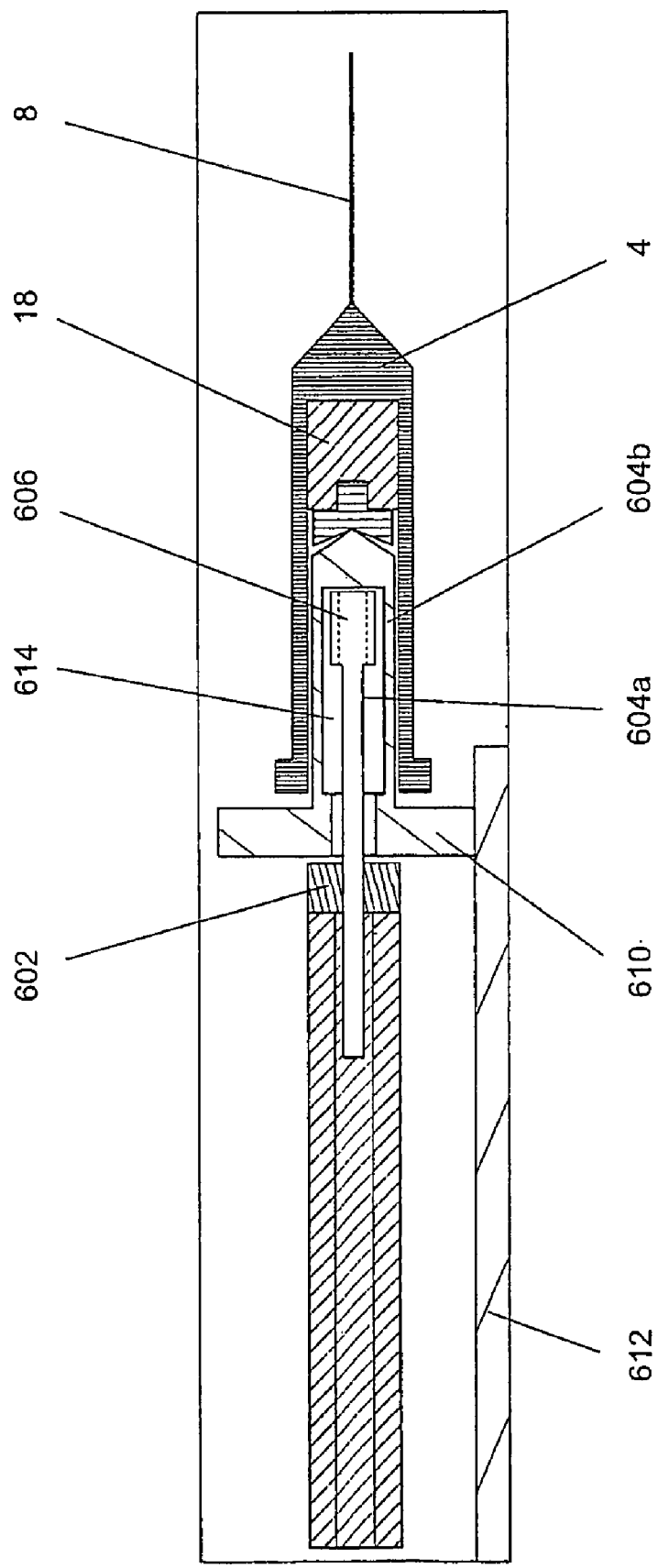

As illustrated in FIG. 20, the overall length of the drive coupling 604b will reduce in length until the non rotatable components 604a has moved to a position in which its male thread disconnects from the female thread of the rotatable portion 604b. At this time, the rotatable portion 604b and the syringe 4 will be released such that the syringe 4 and needle 8 can be retracted as illustrated in FIG. 21. It is merely necessary for the internal hollow section 614 to be of sufficient length to allow full retraction of the needle 8.

The invention claimed is:

1. An injection device including:
   a housing for containing a syringe having a bore extending from an end surface, a needle communicating with the bore through the end surface and a dispensing piston movable in said bore towards said end surface so as to expel the contents of the syringe through the needle, the housing having an opening at one end through which the needle may extend;
   a resilient member for biassing the syringe and needle inwardly of the housing;
   a drive element movable towards said one end so as to move the needle of the syringe out of the opening and to move the dispensing piston of the syringe towards the end surface;
   a mechanism operable to release the syringe such that the needle moves inwardly of the housing;
   a drive coupling for extending from said drive element to the dispensing piston of the syringe so as to transfer movement of said drive element to the dispensing piston;
   wherein the drive coupling is compressible in length such that, after the drive element has moved the dispensing piston to the end surface, the drive coupling gradually reduces in length and transfers sufficient force to maintain the needle in its extended position whilst the dispensing piston is maintained at the end surface until said mechanism releases the syringe.

2. An injection device according to claim 1 wherein the mechanism is operable when the drive element reaches a predetermined position in said housing and the drive coupling gradually reduces in length such that, after the dispensing piston reaches the end surface, the drive element continues to move in said housing to said predetermined position.

3. An injection device according to claim 1 wherein the drive coupling includes:
   a chamber defined between first and second relatively movable walls, the first wall being movable by said drive element and said second wall being operable to move the dispensing piston; and
   a bleed orifice for bleeding flowable material from the chamber.

4. An injection device according to claim 3 wherein the drive coupling includes:
   a main body for mounting on the syringe relative to the bore and the needle, the main body having a bounding wall defining an elongate passage within which the first and second walls are both movable, the chamber being defined by the bounding wall and the first and second walls.

5. An injection device according to claim 4 wherein the bleed orifice is formed at a predetermined longitudinal position along the bounding wall and is only exposed to the chamber once the second wall passes the predetermined longitudinal position.

6. An injection device according to claim 3 including a syringe contained in the housing, the syringe having a bore extending from an end surface, a needle communicating with the bore through the end surface and a dispensing piston movable in said bore towards said end surface so as to expel the contents of the syringe through the needle, wherein:
   the drive coupling is formed in the syringe.

7. An injection device according to claim 6 wherein the first and second walls are movable in said bore and the chamber is defined by the bore and the first and second walls.

8. An injection device according to claim 7 wherein the bleed orifice is formed at a predetermined longitudinal position along the bore and is only opened to the chamber once the second wall passes the predetermined longitudinal position.

9. An injection device according to claim 5 wherein the bleed orifice has a cross-section which is elongated such that, as the second wall moves towards the end surface, flowable material bleeds faster from the chamber.

10. An injection device according to claim 5 further including an array of bleed orifices extending towards said end surface such that, as the second wall moves towards the end surface, flowable material bleeds faster from the chamber.

11. An injection device according to claim I wherein the drive coupling includes:
    a drive frictional surface engaging a driven frictional surface, the drive frictional surface being movable by said drive element and said driven frictional surface being operable to move the dispensing piston such that when the dispensing piston reaches the end surface the drive frictional surface slips relative to the driven frictional surface.

12. An injection device according to claim 11 wherein the drive frictional surface is rotatable about an axis generally perpendicular to the drive frictional surface and is moved by said drive element at a position offset from the axis.

13. An injection device according to claim 11 wherein the driven frictional surface is rotatable about an axis generally perpendicular to the drive frictional surface and is operable to move the dispensing piston from a position offset from the axis.

14. An injection device according to claim 1 wherein the drive coupling includes:
    a rack; and
    a pinion gear;
    wherein one of the rack and the pinion gear is movable by said drive element and the other of the rack and the pinion gear is operable to move the dispensing piston.

15. An injection device according to claim 14 wherein the pinion gear includes a friction brake such that, when the dispensing piston reaches the end surface, the friction brake slips.

16. An injection device according to claim 14 wherein the pinion gear drives a fly wheel such that, when the dispensing piston reaches the end surface, the pinion gear is turned against an inertial resistance of the fly wheel.

17. An injection device according to claim 1 wherein the drive coupling does not reduce in length until the dispensing piston has reached a position at least proximate the end surface.

18. An injection device according to claim 4 wherein the main body is fabricated out of plastic, and the bleed orifice is formed by drilling or in the injection moulding process itself.

19. An injection device according to claim 3 further including an absorbent wicking material to retain material which has escaped from the bleed orifice.

20. A drive coupling for use in an injection device, wherein the injection device comprises a housing for containing a syringe having a bore extending from an end surface, a needle communicating with the bore through the end surface and a dispensing piston movable in said bore towards said end surface so as to expel the contents of the syringe through the needle, the housing having an opening at one end through which the needle may extend; a resilient member for biassing the syringe and needle inwardly of the housing; a drive element movable towards said one end so as to move the needle of the syringe out of the opening and to move the dispensing piston of the syringe towards the end surface; a mechanism operable to release the syringe such that the needle moves inwardly of the housing; a drive coupling for extending from said drive element to the dispensing piston of the syringe so as to transfer movement of said drive element to the dispensing piston; wherein the drive coupling is compressible in length such that, after the drive element has moved the dispensing piston to the end surface, the drive coupling gradually reduces in length and transfers sufficient force to maintain the needle in its extended position whilst the dispensing piston is maintained at the end surface until said mechanism releases the syringe, wherein the drive coupling having:

a length for extending from the drive element to the dispensing piston of the syringe so as to transfer movement of the drive element to the dispensing piston;

wherein the drive coupling is compressible in length whilst overcoming the bias of the resilient member such that, after the drive element has moved the dispensing piston to the end surface, the drive coupling gradually reduces in length whilst the dispensing piston is maintained at the end surface until the mechanism releases the syringe.

21. An injection device according to claim 1 further including:

an engagement for transferring drive directly from the drive coupling to a syringe body of the syringe such that movement of the drive element towards said one end causes no relative movement of the dispensing piston in the syringe;

wherein the engagement is releasable once the needle of the syringe extends out of the opening such that movement of the drive element towards said one end causes relative movement of the dispensing piston in the syringe body.

22. An injection device including:

a housing for containing a syringe having a bore extending in a syringe body from an end surface, a needle communicating with the bore through the end surface and a dispensing piston movable in said bore towards said end surface so as to expel the contents of the syringe through the needle, the housing having an opening at one end through which the needle may extend;

a resilient member for biassing the syringe and needle inwardly of the housing;

a drive element movable towards said one end so as to move the needle of the syringe out of the opening and to move the dispensing piston of the syringe towards the end surface;

a drive coupling for extending from said drive element to the dispensing piston of the syringe so as to transfer movement of said drive element to the dispensing piston, wherein the drive coupling maintains direct connection between the drive element to the dispensing piston; and an engagement for transferring drive directly from the drive coupling to the syringe body such that movement of the drive element towards said one end causes no relative movement of the dispensing piston in the syringe;

wherein the engagement is releasable once the needle of the syringe extends out of the opening such that movement of the drive element towards said one end causes relative movement of the dispensing piston in the syringe body.

23. An injection device according to claim 21 wherein the housing includes a release portion which interacts with the engagement to release drive to the syringe.

24. An injection device according to claim 23 wherein the release portion is located in the housing at a predetermined position and the engagement includes a trigger which is operated by the release portion to release drive to the syringe upon reaching the predetermined position.

25. An injection device according to claim 23 wherein the engagement includes a resilient latch and the resilient portion includes at least a recess in a wall of the housing allowing deflection of the resilient latch to release the drive to the syringe.

26. An injection device according to claim 25 wherein the at least a recess engages the resilient latch so as to prevent further relative movement of the syringe body in the housing.

27. An injection device according to claim 25 wherein the drive coupling includes a fluid chamber defined between first and second relatively movable walls, the first wall being part of a drive coupling piston and the resilient latch operating on the drive coupling piston.

28. An injection device according to claim 23 wherein:

the drive coupling includes a rigid element extending from the drive element;

the engagement includes at least one protrusion on a surface of the rigid element and a latch fixed relative to the syringe body engaging the protrusion; and the release portion includes a stop on the housing for engaging the latch;

wherein the rigid element moves the latch with the protrusion until the latch abuts the stop, whereupon the latch releases from the protrusion.

29. An injection device according to claim 28 wherein the latch is deflected resiliently past the protrusion.

30. An injection device according to claim 28 wherein the latch is hinged as a cantilever at a point between an end engaging the protrusion and an opposite end and wherein the stop deflects the opposite end so as to release engagement with the protrusion.

31. An injection device according to claim 21 wherein the engagement releasably connects the drive coupling to the syringe.

32. An injection device according to claim 21 wherein the engagement releasably connects a part of the drive coupling movable with the drive element to a part of the drive coupling for mounting to the syringe in a fixed relative position to the needle.

33. An injection device according to claim 1 wherein the drive coupling includes a longitudinally extending member, a pinion gear rotatably mounted on said longitudinally extending member and a longitudinally extending rack gear for engagement with the pinion gear.

34. An injection device according to claim 33 wherein features are provided to resist rotation of the pinion gear relative to said longitudinally extending member.

35. An injection device according to claim 34 wherein said features comprise a damper.

36. An injection device according to claim 33 wherein a guide structure is provided to engage with a portion of the pinion gear to prevent rotation of the pinion gear until the pinion gear has travelled past a predetermined longitudinal position in the injection device whereupon the pinion gear starts to rotate and the drive coupling reduces in length.

37. An injection device according to claim 33 wherein the rack gear has a predetermined length such that after a predetermined rotation of the pinion gear, the pinion gear travels beyond an end of the rack gear and said longitudinally extending member and the syringe are released to move inwardly of the housing.

38. An injection device according to claim 1 wherein the drive coupling comprises first and second relatively rotatable members.

39. An injection device according to claim 38 wherein features are provided to resist relative rotation of the first and second members.

40. An injection device according to claim 39 wherein said features comprise a damper.

41. An injection device according to claim 39 wherein said features comprise at least one component for spinning against air resistance.

42. An injection device according to claim 38 wherein a guide structure is provided to engage with at least one of the first and second members so as to prevent relative rotation until the drive coupling has travelled past a predetermined longitudinal position in the device whereupon relative rotation starts and the drive coupling reduces in length.

43. An injection device according to claim 38 wherein the first and second members are joined by corresponding threads such that relative rotation causes the drive coupling to reduce in length.

44. An injection device according to claim 43 wherein the corresponding threads have a predetermined extent such that, after a predetermined amount of relative rotation, the corresponding threads and the first and second members disengage and the syringe is released to move inwardly of the housing.

45. An injection device according to claim 22 wherein the housing includes a release portion which interacts with the engagement to release drive to the syringe.

46. An injection device according to claim 45 wherein the release portion is located in the housing at a predetermined position and the engagement includes a trigger which is operated by the release portion to release drive to the syringe upon reaching the predetermined position.

47. An injection device according to claim 45 wherein the engagement includes a resilient latch and the resilient portion includes at least a recess in a wall of the housing allowing deflection of the resilient latch to release the drive to the syringe.

48. An injection device according to claim 47 wherein the at least a recess engages the resilient latch so as to prevent further relative movement of the syringe body in the housing.

49. An injection device according to claim 47 wherein the drive coupling includes a fluid chamber defined between first and second relatively movable walls, the first wall being part of a drive coupling piston and the resilient latch operating on the drive coupling piston.

50. An injection device according to claim 45 wherein:
the drive coupling includes a rigid element extending from the drive element;
the engagement includes at least one protrusion on a surface of the rigid element and a latch fixed relative to the syringe body engaging the protrusion; and
the release portion includes a stop on the housing for engaging the latch;
wherein the rigid element moves the latch with the protrusion until the latch abuts the stop, whereupon the latch releases from the protrusion.

51. An injection device according to claim 50 wherein the latch is deflected resiliently past the protrusion.

52. An injection device according to claim 50 wherein the latch is hinged as a cantilever at a point between an end engaging the protrusion and an opposite end and wherein the stop deflects the opposite end so as to release engagement with the protrusion.

53. An injection device according to claim 22 wherein the engagement releasably connects the drive coupling to the syringe.

54. An injection device according to claim 22 wherein the engagement releasably connects a part of the drive coupling movable with the drive element to a part of the drive coupling for mounting to the syringe in a fixed relative position to the needle.

55. An injection device according to claim 18 wherein the main body is fabricated out of plastic by injection moulding, and the bleed orifice is formed by mechanical, fluid or laser drilling.

56. An injection device according to claim 1 wherein the drive coupling gradually reduces in length and transfers sufficient force in a direction of the end surface of the syringe to maintain the needle in its extended position whilst the dispensing piston is maintained at the end surface until said mechanism releases the syringe.

57. A drive coupling according to claim 20, wherein the drive coupling gradually reduces in length and transfers sufficient force in a direction of the end surface of the syringe to maintain the needle in its extended position whilst the dispensing piston is maintained at the end surface until said mechanism releases the syringe.

* * * * *

UNITED STATES PATENT AND TRADEMARK OFFICE
CERTIFICATE OF CORRECTION

PATENT NO. : 7,476,217 B2 Page 1 of 1
APPLICATION NO. : 10/513159
DATED : January 13, 2009
INVENTOR(S) : Martin et al.

It is certified that error appears in the above-identified patent and that said Letters Patent is hereby corrected as shown below:

On the Title page, Item (*) Notice should read – Subject to any disclaimer, the term of this patent is extended or adjusted under 35 U.S.C. 154(b) by 407 days.

Signed and Sealed this

First Day of September, 2009

David J. Kappos
*Director of the United States Patent and Trademark Office*

UNITED STATES PATENT AND TRADEMARK OFFICE
CERTIFICATE OF CORRECTION

PATENT NO. : 7,476,217 B2
APPLICATION NO. : 10/513159
DATED : January 13, 2009
INVENTOR(S) : Martin et al.

It is certified that error appears in the above-identified patent and that said Letters Patent is hereby corrected as shown below:

On the cover page,

[*] Notice: Subject to any disclaimer, the term of this patent is extended or adjusted under 35 USC 154(b) by (703) days Delete the phrase "by 407 days" and insert -- by 703 days --

Signed and Sealed this

Sixth Day of April, 2010

David J. Kappos
*Director of the United States Patent and Trademark Office*